US011884681B2

(12) United States Patent
Fleck et al.

(10) Patent No.: US 11,884,681 B2
(45) Date of Patent: Jan. 30, 2024

(54) 3H,4H,5H,6H,7H-PYRIMIDO[4,5-B][1,4]OXAZINE-4,6-DIONE DERIVATIVES AS TRPA1 INHIBITORS

(71) Applicant: Boehringer Ingelheim International GmbH, Ingelheim am Rhein (DE)

(72) Inventors: Martin Thomas Fleck, Munich (DE); Florian Paul Christian Binder, Maselheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/719,430

(22) Filed: Apr. 13, 2022

(65) Prior Publication Data
US 2022/0340593 A1 Oct. 27, 2022

(30) Foreign Application Priority Data

Apr. 14, 2021 (EP) .................................... 21168440

(51) Int. Cl.
*C07D 498/04* (2006.01)
(52) U.S. Cl.
CPC .................................. *C07D 498/04* (2013.01)
(58) Field of Classification Search
None
See application file for complete search history.

(56) References Cited

U.S. PATENT DOCUMENTS

2021/0403482 A1  12/2021  Fleck et al.

FOREIGN PATENT DOCUMENTS

WO  2017060488 A1  4/2017

OTHER PUBLICATIONS

Mukhopadhyay et al (Pharmaceuticals 9:70, 2016) (Year: 2016).*
Bousquet et al., "Nrf2-interacting nutrients and COVID-19: time for research to develop adaptation strategies", Clin Transl Allergy, Dec. 3, 2020, 10(1):58, pp. 1-18.
Bousquet et al., "Spices to Control COVID-19 Symptoms: Yes, but Not Only . . . ", Int Arch Allergy Immunol, 2021, 182(6), pp. 489-495.
Ahamed et al., "In vitro and in vivo evidence for shear-induced activation of latent transforming growth factor-beta1", Blood, Nov. 2008, 112(9), pp. 3650-3660.
Andrade et al., "TRPA1 receptor modulation attenuates bladder overactivity induced by spinal cord injury", Am J Physiol Renal Physiol., May 2011, 300(5), pp. F1223-F1234.
Cevikbas et al., "A sensory neuron-expressed IL-31 receptor mediates T helper cell-dependent itch: Involvement of TRPV1 and TRPA1", J Allergy Clin Immunol., Feb. 2014, 133(2), pp. 448-460.
Chen et al., "Intrathecal administration of TRPA1 antagonists attenuate cyclophosphamide-induced cystitis in rats with hyperreflexia micturition", BMC Urol., Jun. 2016, 16(1):33, pp. 1-9.
Chen et al., "Transient receptor potential ankyrin 1 (TRPA1) antagonists: a patent review (2015-2019)", Expert Opinion on Therapeutic Patents, 2020, vol. 30, No. 9, pp. 643-657.
Conklin et al., "TRPA1 channel contributes to myocardial ischemia-reperfusion injury", Am J Physiol Heart Circ Physiol., Apr. 2019, 316(4), pp. H889-H899.
De Moura et al., "The blockade of transient receptor potential ankirin 1 (TRPA1) signalling mediates antidepressant- and anxiolytic-like actions in mice", Br J Pharmacol., Sep. 2014, 171(18), pp. 4289-4299.
Du et al., "Differential expression profile of cold (TRPA1) and cool (TRPM8) receptors in human urogenital organs", Urology., Aug. 2008, 72(2), pp. 450-455.
Du et al., "Transient receptor potential channel A1 involved in sensory transduction of rat urinary bladder through C-fiber pathway", Urology., Oct. 2007, 70(4), pp. 826-831.
Edelmayer et al., "Activation of TRPA1 on dural afferents: a potential mechanism of headache pain", Pain., Sep. 2012, 153(9), pp. 1949-1958.
Engel et al., "TRPA1 and substance P mediate colitis in mice" Gastroenterology., Oct. 2011, 141(4), pp. 1346-1358.
Froese et al., "Stretch-induced Activation of Transforming Growth Factor-? 1 in Pulmonary Fibrosis", Am J Respir Crit Care Med., Jul. 2016, 194(1), pp. 84-96.
Grace et al., "TRPA1 receptors in cough" Pulm Pharmacol Ther., Jun. 2011, 24(3), pp. 286-288.
Haas et al., "Tooth injury increases expression of the cold sensitive TRP channel TRPA1 in trigeminal neurons", Arch Oral Biol., Dec. 2011, 56(12), pp. 1604-1609.
Hamilton et al., "Proton-gated Ca(2+)-permeable TRP channels damage myelin in conditions mimicking ischaemia", Nature. Jan. 2016, 529(7587):523-527.
Hiyama et al., "TRPA1 sensitization during diabetic vascular impairment contributes to cold hypersensitivity in a mouse model of painful diabetic peripheral neuropathy", Mol Pain., 2018, 14:17, pp. 1-13.
Horvath et al. "Transient receptor potential ankyrin 1 (TRPA1) receptor is involved in chronic arthritis: in vivo study using TRPA1-deficient mice", Arthritis Res Ther., Jan. 2016, 18:6, pp. 1-14.
International Search Report and Written Opinion for corresponding application, PCT/EP2022/059815, dated Jul. 13, 2022.
Koivisto et al., "Transient receptor potential ankyrin 1 (TRPA1) ion channel in the pathophysiology of peripheral diabetic neuropathy", Scand J Pain., Jul. 2013, 4(3), pp. 129-136.
Kremeyer et al., "A gain-of-function mutation in TRPA1 causes familial episodic pain syndrome", Neuron., Jun. 2010, 66(5), pp. 671-680.
Lin et al., "Lung Epithelial TRPA1 Transduces the Extracellular ROS into Transcriptional Regulation of Lung Inflammation Induced by Cigarette Smoke: The Role of Influxed $Ca^2$?", Mediators Inflamm., 2015, 2015:148367, pp. 1-16.

(Continued)

*Primary Examiner* — Craig D Ricci
(74) *Attorney, Agent, or Firm* — Philip I. Datlow

(57) ABSTRACT

The present disclosure provides certain 3H,4H,5H,6H,7H-pyrimido[4,5-b][1,4]oxazine-4,6-dione derivatives that are inhibitors of transient receptor potential ankyrin 1 (TRPA1), and are therefore useful for the treatment of diseases treatable by inhibition of TRPA1. Also provided are pharmaceutical compositions containing the same, and processes for preparing said compounds.

9 Claims, No Drawings

(56) References Cited

OTHER PUBLICATIONS

Liu et al., "TRPA1 controls inflammation and pruritogen responses in allergic contact dermatitis", FASEB J., Sep. 2013, 27(9), pp. 3549-3563.

Matta et al., "General anesthetics activate a nociceptive ion channel to enhance pain and inflammation", Proc Natl Acad Sci U S A., Jun. 2008, 105(25), pp. 8784-8789.

Moilanen et al.,"Urate crystal induced inflammation and joint pain are reduced in transient receptor potential ankyrin 1 deficient mice—potential role for transient receptor potential ankyrin 1 in gout", PLoS One., Feb. 2015, 10(2), pp. 1-13.

Montell, "The TRP superfamily of cation channels" Science's STKE. Feb. 2005, (272):re3, pp. 1-25.

Nummenmaa et al., "Transient receptor potential ankyrin 1 (TRPA1) is functionally expressed in primary human osteoarthritic chondrocytes", Arthritis Res Ther., Aug. 2016, 18(1):185, pp. 1-11.

Oh et al., "TRPA1-dependent pruritus in IL-13-induced chronic atopic dermatitis", J Immunol., Dec. 2013, 191(11), pp. 5371-5382.

Preti et al., "Transient receptor potential ankyrin 1 (TRPA1) antagonists", Pharmaceutical Patent Analyst, 2015, vol. 4, No. 2, pp. 75-94.

Schenkel et al., "Optimization of a Novel Quinazolinone-Based Series of Transient Receptor Potential AI (TRPA1) Antagonists Demonstrating Potent in Vivo Activity", Journal of Medicinal Chemistry, 2016, vol. 59, No. 6, pp. 2794-2809.

Skerratt et al., "Chapter Three Recent Progress in the Discovery and Development of TRPA1 Modulators", Progress in Medicinal Chemistry, 2017, vol. 56, pp. 81-115.

Song et al., "Cough hypersensitivity as a neuro-immune interaction", Clin Transl Allergy., Jul. 2015, 5:24, pp. 1-10.

Trevisan et al., "TRPA1 receptor stimulation by hydrogen peroxide is critical to trigger hyperalgesia and inflammation in a model of acute gout", Free Radic Biol Med., Jul. 2014, 72, 200-209.

Tschumperlin et al., "Mechanical stress triggers selective release of fibrotic mediators from bronchial epithelium", Am J Respir Cell Mol Biol., Feb. 2003, 28(2), pp. 142-149.

Wang et al., "Negative Regulation of TRPA1 by AMPK in Primary Sensory Neurons as a Potential Mechanism of Painful Diabetic Neuropathy. Diabetes", Jan. 2018, 67(1), pp. 98-109.

Wang et al., "Roles of TRPA1 and TRPV1 in cigarette smoke-induced airway epithelial cell injury model", Free Radic Biol Med., Apr. 2019, 134, pp. 229-238.

Wilson et al., "The epithelial cell-derived atopic dermatitis cytokine TSLP activates neurons to induce itch", Cell., Oct. 2013, 155(2), pp. 285-295.

Wilson et al., "The ion channel TRPA1 is required for chronic itch", J Neurosci., May 2013, 33(22), pp. 9283-9294.

Xie et al., "Expression of transforming growth factor-beta (TGF-beta) in chronic idiopathic cough", Respir Res., May 2009, 10(1):40, pp. 1-10.

Yamamoto et al., "Cyclic stretch upregulates interleukin-8 and transforming growth factor-beta1 production through a protein kinase C-dependent pathway in alveolar epithelial cells", Respirology, Jun. 2002, 7(2), pp. 103-109.

* cited by examiner

3H,4H,5H,6H,7H-PYRIMIDO[4,5-B][1,4] OXAZINE-4,6-DIONE DERIVATIVES AS TRPA1 INHIBITORS

FIELD OF THE INVENTION

The present disclosure provides certain 3H,4H,5H,6H, 7H-pyrimido[4,5-b][1,4]oxazine-4,6-dione derivatives that are inhibitors of transient receptor potential ankyrin 1 (TRPA1), and are therefore useful for the treatment of diseases treatable by inhibition of TRPA1. Also provided are pharmaceutical compositions containing the same, and processes for preparing said compounds.

BACKGROUND INFORMATION

Transient receptor potential channels (TRP channels) are a group of voltage-gated ion channels located mostly on the plasma membrane of numerous mammalian cell types. There are approximately 30 structurally related TRP channels sorted into groups: TRPA, TRPC, TRPM, TRPML, TRPN, TRPP and TRPV. Transient receptor potential cation channel, subfamily A, member 1 (TRPA1), also known as transient receptor potential ankyrin 1, is the only member of the TRPA gene subfamily. Structurally, TRPA channels are characterized by multiple N-terminal ankyrin repeats (~14 in the N-terminus of human TRPA1) that gives rise to the "A" for ankyrin designation (Montell, 2005).

TRPA1 is highly expressed in the plasma membrane of sensory neurons in the dorsal root and nodose ganglia that serve both skin and lung, as well as in small intestine, colon, pancreas, skeletal muscle, heart, brain, bladder and lymphocytes (https://www.proteinatlas.org/) as well as in human lung fibroblasts.

TRPA1 is best known as a sensor for environmental irritants giving rise to somatosensory modalities such as pain, cold and itch. TRPA1 is activated by a number of reactive, electrophilic stimuli (e.g. allyl isothiocyanate, reactive oxygen species), as well as non-reactive compounds (e.g. icilin), implicated in cough associated with asthma, chronic pulmonary obstructive disease (COPD), idiopathic pulmonary fibrosis (IPF) or post-viral cough or for chronic idiopathic cough as well as cough in sensitive patients. (Song and Chang, 2015; Grace and Belvisi, 2011). TRPA1 inhibitors are useful in the treatment of IPF in which cough is highly prevalent because of the link between cough and lung injury, based on studies showing cough-induced elevation of TGF-β (Xie et al., 2009; Froese et al., 2016; Tschumperlin et al., 2003; Yamamoto et al., 2002; Ahamed et al., 2008). Acute lung injury as a result of SARS-Cov-2 infection is mediated at least in part via reactive oxygen species (ROS). ROS are a direct activator of TRPA1. Furthermore, desensitisation of TRPA1 via consumption of spicy foods has been postulated to regulate the Nrf2 pathway and reduce oxidative stress (Bousquet et al., 2020, Bousquet et al., 2021). TRPA1 inhibitors therefore have the potential in the treatment of Covid-19/SARS-Cov-2 induced lung injury. TRPA1 antagonists inhibit calcium signaling triggered by cough triggers such as cigarette smoke extract (CSE) oxidative stress, inflammatory mediator release and downregulated antioxidant gene expression (Lin et al., 2015; Wang et al., 2019). TRPA1 antagonists are effective in studies of atopic dermatitis (Oh et al., 2013; Wilson et al., 2013), contact dermatitis (Liu et al., 2013), psoriasis-associated itch (Wilson et al., 2013) and IL-31-dependent itch (Cevikbas et al., 2014). A human TRPA1 gain-of-function has been associated with familial episodic pain syndrome (Kremeyer et al., 2010).

A TRPA1 antagonist was effective in a behavioral model of migraine-related allodynia (Edelmayer et al., 2012). TRPA1 is selectively increased in trigeminal ganglia innervating injured teeth when compared to TRPA1 expression in trigeminal ganglia innervating healthy teeth (Haas et al., 2011). Several anaesthetics are known to be TRPA1 agonists, including isoflurane (Matta et al., 2008) providing rationale for TRPA1 inhibitors for the relief of post-surgical pain. TRPA1 knockout mice and wild type mice treated with a TRPA1 antagonist showed anxiolytic- and antidepressant-like phenotypes (de Moura et al., 2014). TRPA1 inhibitors are expected to have benefit in the treatment of diabetic neuropathy based on studies showing a mechanistic link of inverse regulation between AMPK and TRPA1 (Hiyama et al., 2018; Koivisto and Pertovaara, 2013; Wang et al., 2018). TRPA1 knockout mice exhibit smaller myocardial infarct sizes compared to wild type mice (Conklin et al., 2019). TRPA1 knockout and pharmacological intervention inhibited TNBS-induced colitis in mice (Engel et al., 2011). In a mouse brain ischaemia model, TRPA1 knock-out and TRPA1 antagonists reduce myelin damage (Hamilton et al., 2016). Urate crystals and joint inflammation are reduced in TRPA1 knockout mice in a monosodium urate mouse model of gout (Moilanen et al., 2015). TRPA1 deletion in rats ameliorated joint inflammation and hyperalgesia in a rat model of acute gout flares (Trevisan et al., 2014). Activation of TRPA1 elicits an inflammatory response in osteoarthritic chondrocytes (Nummenmaa et al., 2016). TRPA1 inhibition and genetic deletion reduces inflammatory mediators in osteoarthritic mouse chondrocytes and murine cartilage (Nummenmaa et al., 2016). Finally, TRPA1 knockout mice exhibited improvements in weight bearing on the osteoarthritic limb in an MIA-evoked knee swelling model (Horvath et al., 2016). TRPA1 is differentially expressed in the bladder epithelium of rats (Du et al., 2007) and of patients with bladder outlet obstruction (Du et al., 2008). TRPA1 receptor modulation attenuates bladder overactivity in a rat model of spinal cord injury (Andrade et al., 2011) and intrathecal administration of TRPA1 antagonists attenuate cyclophosphamide-induced cystitis in rats with hyper-reflexia micturition (Chen et al., 2016).

It is therefore desirable to provide potent TRPA1 inhibitors.

TRPA1 inhibitors of various structural classes are reviewed in S. Skerratt, Progress in Medicinal Chemistry, 2017, Volume 56, 81-115 and in D. Preti, G. Saponaro, A. Szallasi, Pharm. Pat. Anal. (2015) 4 (2), 75-94, and in H. Chen, Transient receptor potential ankyrin 1 (TRPA1) antagonists: a patent review (2015-2019), Expert Opin Ther Pat., 2020.

WO2017/060488 discloses compounds that are antagonists of TRPA1, having the generalized structural formula

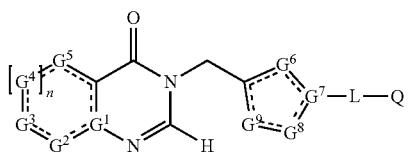

The TRPA1 activities of Examples 53, 72, 73, 86 and 90 therein are disclosed having IC50's of less than 100 nM in a calcium flux assay.

L. Schenkel, et al., J. Med. Chem. 2016, 59, 2794-2809 discloses quinazolinone-based TRPA1 antagonists including compounds of the generalized structural formula

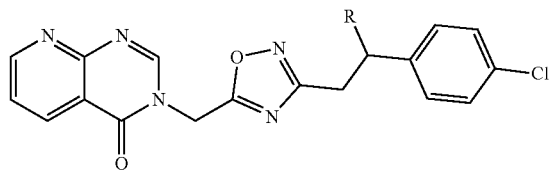

of which compound 31, wherein R is OH, is disclosed as having an antagonistic TRPA1 activity of $IC_{50}$ 58 nM in a FLIPR assay and having an intrinsic clearance in human liver microsomes of <14 µL/min/kg.

DETAILED DESCRIPTION OF THE INVENTION

The present invention discloses novel 3H,4H,5H,6H,7H-pyrimido[4,5-b][1,4]oxazine-4,6-dione derivatives that are inhibitors of transient receptor potential ankyrin 1 (TRPA1), possessing appropriate pharmacological and pharmacokinetic properties enabling their use as medicaments for the treatment of conditions and/or diseases treatable by inhibition of TRPA1.

The compounds of the present invention may provide several advantages, such as enhanced potency, high metabolic and/or chemical stability, high selectivity, safety and tolerability, enhanced solubility, enhanced permeability, desirable plasma protein binding, enhanced bioavailability, suitable pharmacokinetic profiles, and the possibility to form stable salts.

The Compounds of the Invention

The present invention provides 3H,4H,5H,6H,7H-pyrimido[4,5-b][1,4]oxazine-4,6-dione derivatives that are surprisingly potent inhibitors of TRPA1 (Assay A), further characterised by
improved stability in human liver microsomes (Assay B)
improved stability in human hepatocytes (Assay C).

Compounds of the present invention differ structurally from examples 53, 72, 73, 86 and 90 in WO2017/060488 and from example 31 in L. Schenkel, et al., J. Med. Chem. 2016, 59, 2794-2809, in that they contain a substituted 3H,4H,5H,6H,7H-pyrimido[4,5-b][1,4]oxazine-4,6-dione core as well as substituents adjacent to a secondary aliphatic alcohol. These structural differences unexpectedly lead to a favourable combination of (i) inhibition of TRPA1, (ii) stability in human liver microsomes, and (iii) stability in human hepatocytes.

Stability in human liver microsomes refers to the susceptibility of compounds to biotransformation in the context of selecting and/or designing drugs with favorable pharmacokinetic properties as a first screening step. The primary site of metabolism for many drugs is the liver. Human liver microsomes contain the cytochrome P450s (CYPs), and thus represent a model system for studying phase I drug metabolism in vitro. Enhanced stability in human liver microsomes is associated with several advantages, including increased bioavailability and adequate half-life, which can enable lower and less frequent dosing of patients. Thus, enhanced stability in human liver microsomes is a favorable characteristic for compounds that are to be used for drugs. Therefore, compounds of the present invention in addition to being able to inhibit TRPA1 are expected to have a favorable in vivo clearance and thus the desired duration of action in humans.

Stability in human hepatocytes refers to the susceptibility of compounds to biotransformation in the context of selecting and/or designing drugs with favorable pharmacokinetic properties. The primary site of metabolism for many drugs is the liver. Human hepatocytes contain the cytochrome P450s (CYPs) and other drug metabolizing enzymes, and thus represent a model system for studying drug metabolism in vitro. (Importantly, in contrast to liver microsomes assay, the hepatocytes assay covers also phase II biotransformations as well as liver-specific transporter-mediated processes, and therefore represents a more complete system for drug metabolism studies) Enhanced stability in human hepatocytes is associated with several advantages, including increased bioavailability and adequate half-life, which can enable lower and less frequent dosing of patients. Thus, enhanced stability in human hepatocytes is a favorable characteristic for compounds that are to be used for drugs.

The present invention provides novel compounds according to formula (I)

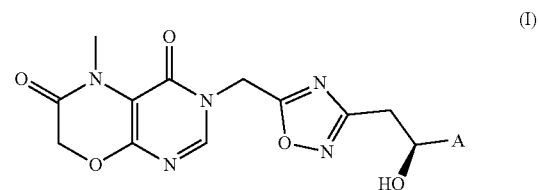

wherein
A is selected from the group consisting of phenyl, thiophenyl, benzofuranyl and benzothiophenyl, and wherein A is unsubstituted or substituted with one or two members of the group $R^1$ consisting of halogen and $C_{1-4}$-alkyl.

Another embodiment of the present invention relates to a compound of formula (I) wherein A is selected from the group consisting of phenyl, thiophenyl, benzofuranyl and benzothiophenyl, and wherein A is unsubstituted or substituted with one or two members of the group $R^1$ consisting of F, Cl, I and $CH_3$.

Another embodiment of the present invention relates to a compound of formula (I) wherein A is selected from the group consisting of phenyl, benzofuranyl and benzothiophenyl, and wherein A is unsubstituted or substituted with one or two members of the group $R^1$ consisting of F, Cl, I and $CH_3$.

Another embodiment of the present invention relates to a compound of formula (I) wherein A is selected from the group consisting of

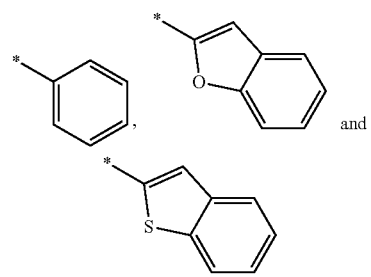

and wherein A is unsubstituted or substituted with one or two members of the group R¹, and R¹ is defined as in any of the preceding embodiments.

Preferred is the compound according to formula (I) selected from the group consisting of

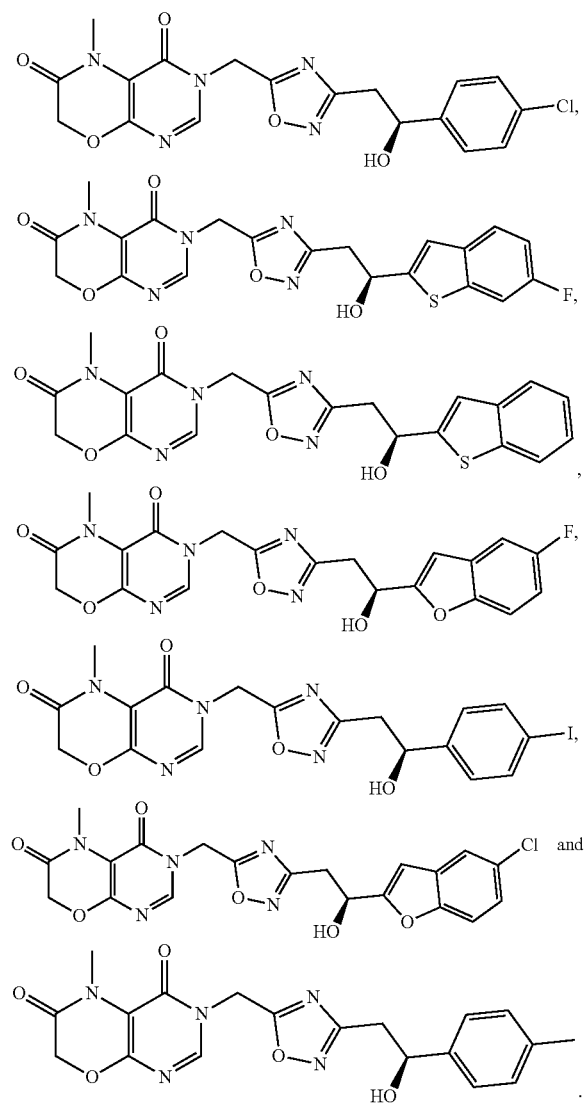

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO, $H_2N$, (O)S, (O)$_2$S, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk may be used in sub-formulas to indicate the bond which is connected to the core molecule as defined.

The numeration of the atoms of a substituent starts with the atom that is closest to the core or to the group to which the substituent is attached.

For example, the term "3-carboxypropyl-group" represents the following substituent:

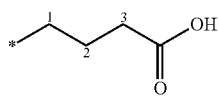

wherein the carboxy group is attached to the third carbon atom of the propyl group. The terms "1-methylpropyl-", "2,2-dimethylpropyl-" or "cyclopropylmethyl-" group represent the following groups:

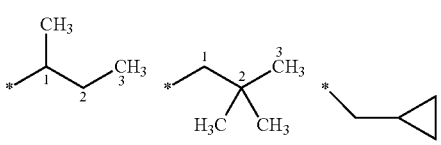

The asterisk may be used in sub-formulas to indicate the bond that is connected to the core molecule as defined.

The term "$C_{1-n}$-alkyl", wherein n is an integer selected from 2, 3, 4 or 5, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "fluoro" added to an "alkyl", "alkylene" or "cycloalkyl" group (saturated or unsaturated) means such a alkyl or cycloalkyl group wherein one or more hydrogen atoms are replaced by a fluorine atom. Examples include, but are not limited to: $H_2FC$—, $HF_2C$— and $F_3C$—.

The term phenyl refers to the radical of the following ring

The term thiophenyl refers to the radical of the following ring

The term benzofuranyl refers to the radical of the following ring

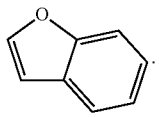

The term benzothiophenyl refers to the radical of the following ring

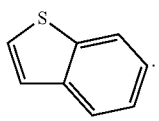

The term 3H,4H,5H,6H,7H-pyrimido[4,5-b][1,4]oxazine-4,6-dione refers to the radical of the following core

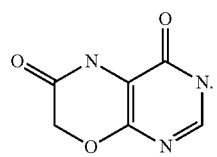

The term "substituted" as used herein, means that any one or more hydrogens on the designated atom is replaced with a selection from the indicated group, provided that the designated atom's normal valence is not exceeded, and that the substitution results in a stable compound.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use without excessive toxicity, irritation, allergic response, or other problem or complication, and commensurate with a reasonable benefit/risk ratio.

As used herein, "pharmaceutically acceptable salt" refers to derivatives of the disclosed compounds wherein the parent compound forms a salt or a complex with an acid or a base. Examples of acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Examples for cations and bases forming a pharmaceutically acceptable salt with a parent compound containing an acidic moiety include $Na^+$, $K^+$, $Ca^{2+}$, $Mg^{2+}$, $NH_4^+$, L-arginine, 2,2'-iminobisethanol, L-lysine, N-methyl-D-glucamine or tris(hydroxymethyl)-aminomethane. The pharmaceutically acceptable salts of the present invention can be synthesized from the parent compound that contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetate salts,) also comprise a part of the present invention.

Biological Assays

Evaluation of TRPA1 Activity

Assay A: TRPA1 Assay

The activity of the compounds of the invention may be demonstrated using the following in vitro TRPA1 cell assay:

Method:

A human HEK293 cell line over-expressing the human TRPA1 ion channel (Perkin Elmer, Product No. AX-004-

PCL) is used as a test system for compound efficacy and potency. Compound activity is determined by measuring the effect of compounds on intracellular calcium concentration induced by AITC (Allylisothiocyanat) agonism in a FLIPRtetra system (Molecular Devices).

Cell Culture:

The cells are obtained as frozen cells in cryo-vials and stored until use at −150° C. Cells are grown in culture medium (MEM/EBSS medium with 10% FCS and 0.4 mg/ML Geneticin). It is important that density does not exceed 90% confluence. For sub-culturing cells are detached from flasks by Versene. At the day before the assay, cells are detached, washed twice with medium (MEM/EBSS medium with 10% FCS) and 20000 cells in 20 µl/well are seeded to Poly D-Lysin biocoated 384-well plates (black, clear bottom, Cat. 356697) from Corning. Plates are incubated for 24 hours at 37° C./5% CO2 before use in the assay.

Compound Preparation

The test compounds are dissolved in 100% DMSO at a concentration of 10 mM and in a first step diluted in DMSO to a concentration of 5 mM, followed by serial dilution steps in 100% DMSO. Dilution factor and number of dilution steps may vary according to needs. Typically 8 different concentrations by 1:5 dilutions are prepared, further intermediate dilutions (1:20) of the substances are carried out with HBSS/HEPES buffer (1×HEPES, Cat. 14065 from Gibco, 20 mM HEPES, Cat. 83264 from SIGMA, 0.1% BSA Cat. 11926 from Invitrogen, pH 7.4

FLIPR Assay:

At the assay day cells are washed 3× with assay puffer, 20 µL buffer remaining in the wells after washing. 10 µL Ca6 kit (Cat. R8191 MolecularDevices) loading buffer in HBSS/HEPES is added to the cells and the plates are incubated with lid for 120 minutes at 37°/5% CO2. 10 µL of compound or controls in HBSS/HEPES buffer/5% DMSO from the intermediate dilution plate are carefully added to the wells Luminescence (indicating the calcium influx or release) is read on the FLIPRtetra device for 10 minutes to monitor the compound induced effects (e.g. agonism). Finally 10 µL of the agonist AITC 50 µM dissolved in HBSS/HEPES buffer/ 0.05% DMSO (final concentration 10 µM) is added to the wells followed by an additional read on the FLIPRtetra device for 10 minutes. The area under the signal curve (AUC) after AITC addition is used for IC50/% inhibition calculations Data Evaluation and Calculation:

Each assay microtiter plate contains wells with vehicle (1% DMSO) controls instead of compound as controls for AITC induced luminescence (100% CTL; high controls) and wells with vehicle controls without AITC as controls for non-specific changes in luminescence (0% CTL; low controls).

The analysis of the data is performed by the calculation of the area under signal curve of the individual wells. Based on this values the % value for the measurement of each substance concentration is calculated (AUC(sample)−AUC (low))*100/(AUC(high)−AUC(low)) using MegaLab software (in house development). The IC50 values are calculated from the % control values using MegaLab software. Calculation: $[y=(a-d)/(1+(x/c)^b)+d]$, a=low value, d=high value; x=conc M; c=IC50 M; b=hill; y=% ctrl

TABLE 1

Biological data for compounds of the invention as obtained in Assay A

| Example | hTRPA1 IC$_{50}$ [nM] |
|---|---|
| 1 | 57 |
| 2 | 12 |
| 3 | 27 |
| 4 | 39 |
| 5 | 39 |
| 6 | 51 |
| 7 | 120 |

TABLE 2

Biological data for prior art compounds (examples 53, 72, 73, 86, 90 in WO2017/060488) as obtained in Assay A.

| Example in WO2017/060488 | hTRPA1 IC$_{50}$ [nM] |
|---|---|
| 53 | 36 |
| 72 | 14 |
| 73 | 28 |
| 86 | 67 |
| 90 | 41 |

TABLE 3

Biological data for prior art compounds (example 31 in L. Schenkel, et al., J. Med. Chem. 2016, 59, 2794-2809) as obtained in Assay A.

| Example in Med. Chem. 2016, 59, 2794-2809 | hTRPA1 IC$_{50}$ [nM] |
|---|---|
| 31 | 52 |

Evaluation of Microsomal Clearance

Assay B: Microsomal Clearance:

The metabolic degradation of the test compound is assayed at 37° C. with pooled liver microsomes. The final incubation volume of 100 µl per time point contains TRIS buffer pH 7.6 at RT (0.1 M), magnesium chloride (5 mM), microsomal protein (1 mg/ml) and the test compound at a final concentration of 1 µM.

Following a short preincubation period at 37° C., the reactions are initiated by addition of beta-nicotinamide adenine dinucleotide phosphate, reduced form (NADPH, 1 mM) and terminated by transferring an aliquot into solvent after different time points (0, 5, 15, 30, 60 min). Additionally, the NADPH-independent degradation is monitored in incubations without NADPH, terminated at the last time point. The [%] remaining test compound after NADPH independent incubation is reflected by the parameter c(control) (metabolic stability). The quenched incubations are pelleted by centrifugation (10000 g, 5 min).

An aliquot of the supernatant is assayed by LC-MS/MS for the amount of parent compound. The half-life (t1/2 INVITRO) is determined by the slope of the semilogarithmic plot of the concentration-time profile.

The intrinsic clearance (CL_INTRINSIC) is calculated by considering the amount of protein in the incubation:

$$CL\_INTRINSIC\ [\mu l/min/mg\ protein] = (Ln\ 2/(half-life\ [min]*protein\ content\ [mg/ml]))*1000$$

CL_INTRINSIC_INVIVO [ml/min/kg]=(CL_INTRINSIC [µL/min/mg protein]×MPPGL [mg protein/g liver]×liver factor [g/kg bodyweight])/1000

Qh [%]=CL [ml/min/kg]/hepatic blood flow [ml/min/kg])

Hepatocellularity, human: 120×10e6 cells/g liver
Liver factor, human 25.7 g/kg bodyweight
Blood flow, human 21 ml/(min×kg)

TABLE 4

Biological data for compounds of the invention as obtained in Assay B

| Example | human LM [% Qh] |
|---|---|
| 1 | <23 |
| 2 | <23 |
| 3 | <23 |
| 4 | <23 |
| 5 | 29 |
| 6 | 56 |
| 7 | <23 |

TABLE 5

Biological data for prior art compounds (examples 53, 72, 73, 86, 90 in WO2017/060488) as obtained in Assay B.

| Example in WO2017/060488 | human LM [% Qh] |
|---|---|
| 53 | <23 |
| 72 | 30 |
| 73 | 38 |
| 86 | <23 |
| 90 | 39 |

TABLE 6

Biological data for prior art compounds (example 31 in L. Schenkel, et al., J. Med. Chem. 2016, 59, 2794-2809) as obtained in Assay B.

| Example in Med. Chem. 2016, 59, 2794-2809 | human LM [% Qh] |
|---|---|
| 31 | <23 |

Evaluation of Hepatocyte Clearance

Assay C: Hepatocyte Clearance

The metabolic degradation of the test compound is assayed in a hepatocyte suspension. Hepatocytes (cryopreserved) are incubated in Dulbecco's modified eagle medium (supplemented with 3.5 µg glucagon/500 mL, 2.5 mg insulin/500 mL and 3.75 mg/500 mL hydrocortison) containing 5% species serum.

Following a 30 min preincubation in an incubator (37° C., 10% CO2) 5 µl of test compound solution (80 µM; from 2 mM in DMSO stock solution diluted 1:25 with medium) are added into 395 µl hepatocyte suspension (cell density in the range 0.25-5 Mio cells/mL depending on the species, typically 1 Mio cells/mL; final concentration of test compound 1 µM, final DMSO concentration 0.05%).

The cells are incubated for six hours (incubator, orbital shaker) and samples (25 µl) are taken at 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended.

Decline of parent compound is analyzed by HPLC-MS/MS

CLint is calculated as follows CL_INTRINSIC=Dose/AUC=(C0/CD)/(AUD+clast/k)×1000/60. C0: initial concentration in the incubation [µM], CD: cell density of vital cells [10e6cells/mL], AUD: area under the data [µM×h], clast: concentration of last data point [µM], k: slope of the regression line for parent decline [h−1].

The calculated in vitro hepatic intrinsic clearance can be scaled up to the intrinsic in vivo hepatic Clearance and used to predict hepatic in vivo blood clearance (CL) by the use of a liver model (well stirred model).

CL_INTRINSIC_INVIVO [ml/min/kg]=(CL_INTRINSIC [µL/min/10e6cells]×hepatocellularity [10e6 cells/g liver]×liver factor [g/kg bodyweight])/1000

CL [ml/min/kg]=CL_INTRINSIC_INVIVO [ml/min/kg]×hepatic blood flow [ml/min/kg]/(CL_INTRINSIC_INVIVO [ml/min/kg]+hepatic blood flow [ml/min/kg])

Qh [%]=CL [ml/min/kg]/hepatic blood flow [ml/min/kg])

Hepatocellularity, human: 120×10e6 cells/g liver
Liver factor, human 25.7 g/kg bodyweight
Blood flow, human 21 ml/(min×kg)

TABLE 7

Biological data for compounds of the invention as obtained in Assay C

| Example | human Hepatocytes [% Qh] |
|---|---|
| 1 | 9 |
| 2 | 34 |
| 3 | 31 |
| 4 | 22 |
| 5 | 22 |
| 6 | 37 |
| 7 | 9 |

TABLE 8

Biological data for prior art compounds (examples 53, 72, 73, 86, 90 in WO2017/060488) as obtained in Assay C.

| Example in WO2017/060488 | human Hepatocytes [% Qh] |
|---|---|
| 53 | 25 |
| 72 | 50 |
| 73 | 36 |
| 86 | 12 |
| 90 | 61 |

TABLE 9

Biological data for prior art compounds (example 31 in L. Schenkel, et al., J. Med. Chem. 2016, 59, 2794-2809) as obtained in Assay C.

| Example in Med. Chem. 2016, 59, 2794-2809 | human Hepatocytes [% Qh] |
|---|---|
| 31 | 73 |

Evaluation of Permeability

Caco-2 cells ($1-2\times10^5$ cells/1 cm$^2$ area) are seeded on filter inserts (Costar transwell polycarbonate or PET filters, 0.4 µm pore size) and cultured (DMEM) for 10 to 25 days. Compounds are dissolved in appropriate solvent (like DMSO, 1-20 mM stock solutions). Stock solutions are diluted with HTP-4 buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4\times$7H$_2$O, 0.41 mM NaH$_2$PO$_4\times$H$_2$O, 15 mM HEPES, 20 mM glucose, 0.25% BSA, pH 7.2) to prepare the transport solutions (0.1-300 µM compound, final DMSO<=0.5%). The transport solution (TL) is applied to the apical or basolateral donor side for measuring A-B or B-A permeability (3 filter replicates), respectively. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Evaluation of Plasma Protein Binding

This equilibrium dialysis (ED) technique is used to determine the approximate in vitro fractional binding of test compounds to plasma proteins. Dianorm Teflon dialysis cells (micro 0.2) are used. Each cell consists of a donor and an acceptor chamber, separated by an ultrathin semipermeable membrane with a 5 kDa molecular weight cutoff. Stock solutions for each test compound are prepared in DMSO at 1 mM and diluted to a final concentration of 1.0 µM. The subsequent dialysis solutions are prepared in pooled human or rat plasma (with NaEDTA) from male and female donors. Aliquots of 200 µL dialysis buffer (100 mM potassium phosphate, pH 7.4) are dispensed into the buffer chamber. Aliquots of 200 µL test compound dialysis solution are dispensed into the plasma chambers. Incubation is carried out for 2 hours under rotation at 37° C. At the end of the dialysis period, the dialysate is transferred into reaction tubes. The tubes s for the buffer fraction contain 0.2 mL ACN/water (80/20). Aliquots of 25 µL of the plasma dialysate are transferred into deep well plates and mixed with 25 µL ACN/water (80/20), 25 µL buffer, 25 µL calibration solution and 25 µL Internal Standard solution. Protein precipitation is done by adding 200 µL ACN. Aliquots of 50 µL of the buffer dialysate are transferred into deep well plates and mixed with 25 µL blank plasma, 25 µL Internal Standard solution and 200 µL ACN. Samples are measured on HPLC-MS/MS-Systems and evaluated with Analyst-Software. Percent bound is calculated with the formula: % bound=(plasma concentration−buffer concentration/plasma concentration)×100.

Evaluation of Solubility

Saturated solutions are prepared in well plates (format depends on robot) by adding an appropriate volume of selected aqueous media (typically in the range of 0.25-1.5 ml) into each well which contains a known quantity of solid drug substance (typically in the range 0.5-5.0 mg). The wells are shaken or stirred for a predefined time period (typically in a range of 2-24 h) and than filtered using appropriate filter membranes (typically PTFE-filters with 0.45 µm pore size). Filter absorption is avoided by discarding the first few drops of filtrate. The amount of dissolved drug substance is determined by UV spectroscopy. In addition the pH of the aqueous saturated solution is measured using a glass-electrode pH meter.

Evaluation of Pharmacokinetic Characteristics

The test compound is administered either intravenously or orally to the respective test species. Blood samples are taken at several time points post application of the test compound, anticoagulated and centrifuged.

The concentration of analytes—the administered compound and/or metabolites—are quantified in the plasma samples. PK parameters are calculated using non compartment methods. AUC and Cmax are normalized to a dose of 1 µmol/kg.

Evaluation of Metabolism in Human Hepatocytes In Vitro

The metabolic pathway of a test compound is investigated using primary human hepatocytes in suspension. After recovery from cryopreservation, human hepatocytes are incubated in Dulbecco's modified eagle medium containing 5% human serum and supplemented with 3.5 µg glucagon/500 ml, 2.5 mg insulin/500 ml and 3.75 mg/500 ml hydrocortisone.

Following a 30 min preincubation in a cell culture incubator (37° C., 10% CO$_2$), test compound solution is spiked into the hepatocyte suspension to obtain a final cell density of $1.0*10^6$ to $4.0*10^6$ cells/ml (depending on the metabolic turnover rate of the compound observed with primary human hepatocytes), a final test compound concentration of 10 µM, and a final DMSO concentration of 0.05%.

The cells are incubated for six hours in a cell culture incubator on a horizontal shaker, and samples are removed from the incubation after 0, 0.5, 1, 2, 4 or 6 hours, depending on the metabolic turnover rate. Samples are quenched with acetonitrile and pelleted by centrifugation. The supernatant is transferred to a 96-deepwell plate, evaporated under nitrogen and resuspended prior to bioanalysis by liquid chromatography-high resolution mass spectrometry for identification of putative metabolites.

The structures are assigned tentatively based on Fourier-Transform-MS$^n$ data. Metabolites are reported as percentage of the parent in human hepatocyte incubation with a threshold of ≥4%.

Method of Treatment

The present invention is directed to compounds of general formula 1 which are useful in the prevention and/or treatment of a disease and/or condition associated with or modulated by TRPA1 activity, including but not limited to the treatment and/or prevention of fibrotic disease, inflammatory and immunoregulatory disorders, respiratory or gastrointestinal diseases or complaints, ophthalmic diseases, inflammatory diseases of the joints and inflammatory diseases of the nasopharynx, eyes, and skin and pain and neurological disorders. Said disorders, diseases and complaints include cough, idiopathic pulmonary fibrosis, other pulmonary interstitial diseases and other fibrotic, asthma or allergic diseases, eosinophilic diseases, chronic obstructive pulmonary disease, as well as inflammatory and immunoregulatory disorders, such as rheumatoid arthritis and atherosclerosis, as well as pain and neurological disorders, such as acute pain, surgical pain, chronic pain and depression and bladder disorders.

The compounds of general formula 1 are useful for the prevention and/or treatment of:

(1) Cough such as chronic idiopathic cough or chronic refractory cough, cough associated with asthma, COPD, lung cancer, post-viral infection and idiopathic pulmonary fibrosis and other pulmonary interstitial diseases.

(2) Pulmonary fibrotic diseases such as pneumonitis or interstitial pneumonitis associated with collagenosis, e.g. lupus erythematodes, systemic scleroderma, rheumatoid arthritis, polymyositis and dermatomysitis, idiopathic interstitial pneumonias, such as pulmonary lung fibrosis (IPF), non-specific interstitial pneumonia, respiratory bronchiolitis associated interstitial lung disease, desquamative interstitial pneumonia, cryptogenic orgainizing pneumonia, acute interstitial pneumonia and lymphocytic interstitial pneumonia, lymangioleiomyomatosis, pulmonary alveolar proteinosis, Langerhan's cell histiocytosis, pleural parenchymal fibroelastosis, interstitial lung diseases of known cause, such as interstitial pneumonitis as a result of occupational exposures such as asbestosis, silicosis, miners lung (coal dust), farmers lung (hay and mould), Pidgeon fanciers lung (birds) or other occupational airbourne triggers such as metal dust or mycobacteria, or as a result of treatment such as radiation, methotrexate, amiodarone, nitrofurantoin or chemotherapeutics, or for granulomatous disease, such as granulomatosis with polyangitis, Churg-Strauss syndrome, sarcoidosis, hypersensitivity pneumonitis, or interstitial pneumonitis caused by different origins, e.g. aspiration, inhalation of toxic gases, vapors, bronchitis or pneumonitis or interstitial pneumonitis caused by heart failure, X-rays, radiation, chemotherapy, M. boeck or sarcoidosis, granulomatosis, cystic fibrosis or mucoviscidosis, alpha-1-antitrypsin deficiency, acute lung injury as a result of Covid-19/SARS-Cov-2 infection or pulmonary fibrosis secondary to Covid-19/SARS-Cov-2 infection.

(3) Other fibrotic diseases such as hepatic bridging fibrosis, liver cirrhosis, non-alcoholic steatohepatitis (NASH), atrial fibrosis, endomyocardial fibrosis, old myocardial infarction, glial scar, arterial stiffness, arthrofibrosis, Dupuytren's contracture, keloid, scleroderma/systemic sclerosis, mediastinal fibrosis, myelofibrosis, Peyronie's disease, nephrogenic systemic fibrosis, retroperitoneal fibrosis, adhesive capsulitis.

(4) Inflammatory, auto-immune or allergic diseases and conditions such as allergic or non-allergic rhinitis or sinusitis, chronic sinusitis or rhinitis, nasal polyposis, chronic rhinosinusitis, acute rhinosinusitis, asthma, pediatric asthma, allergic bronchitis, alveolitis, hyperreactive airways, allergic conjunctivitis, bronchiectasis, adult respiratory distress syndrome, bronchial and pulmonary edema, bronchitis or pneumonitis, eosinophilic cellulites (e.g., Well's syndrome), eosinophilic pneumonias (e.g., Loeffler's syndrome, chronic eosinophilic pneumonia), eosinophilic fasciitis (e. g., Shulman's syndrome), delayed-type hypersensitivity, non-allergic asthma; exercise induced bronchoconstriction; chronic obstructive pulmonary disease (COPD), acute bronchitis, chronic bronchitis, cough, pulmonary emphysema; systemic anaphylaxis or hypersensitivity responses, drug allergies (e.g., to penicillin, cephalosporin), eosinophiliamyalgia syndrome due to the ingestion of contaminated tryptophan, insect sting allergies; autoimmune diseases, such as rheumatoid arthritis, Graves' disease, Sjogren's syndrome psoriatic arthritis, multiple sclerosis, systemic lupus erythematosus, myasthenia gravis, immune thrombocytopenia (adult ITP, neonatal thrombocytopenia, pediatric ITP), immune hemolytic anemia (auto-immune and drug induced), Evans syndrome (platelet and red cell immune cytopaenias), Rh disease of the newborn, Goodpasture's syndrome (anti-GBM disease), Celiac, autoimmune cardio-myopathy juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e. g., necrotizing, cutaneous, and hypersensitivity vasculitis); erythema nodosum; eosinophilic myositis, eosinophilic fasciitis, cancers with leukocyte infiltration of the skin or organs; ophthalmic diseases such as age related macular degeneration, diabetic retinopathy and diabetic macular edema, keratitis, eosinophilic keratitis, keratoconjunctivitis, vernal keratoconjunctivitis, scarring, anterior segment scarring, blepharitis, blepharoconjunctivitis, bullous disorders, cicatricial pemphigoid, conjunctival melanoma, papillary conjunctivitis, dry eye, episcleritis, glaucoma, gliosis, Granuloma annulare, Graves' ophthalmopathy, intraocular melanoma, Pinguecula, proliferative vitreoretinopathy, pterygia, scleritis, uveitis, acute gout flares, gout or osteoarthritis.

(5) Pain such as chronic idiopathic pain syndrome, neuropathic pain, dysesthesia, allodynia, migraine, dental pain and post-surgical pain.

(6) Depression, anxiousness, diabetic neuropathy and bladder disorders such as bladder outlet obstruction, overactive bladder, cystitis; myocardial reperfusion injury or brain ischaemia injury.

Accordingly, the present invention relates to a compound of general formula 1 for use as a medicament.

Furthermore, the present invention relates to the use of a compound of general formula 1 for the treatment and/or prevention of a disease and/or condition associated with or modulated by TRPA1 activity.

Furthermore, the present invention relates to the use of a compound of general formula 1 for the treatment and/or prevention of fibrotic disease, inflammatory and immunoregulatory disorders, respiratory or gastrointestinal diseases or complaints, ophthalmic diseases, inflammatory diseases of the joints and inflammatory diseases of the nasopharynx, eyes, and skin, pain and neurological disorders. Said disorders, diseases and complaints include cough, idiopathic pulmonary fibrosis, other pulmonary interstitial diseases and other fibrotic, asthma or allergic diseases, eosinophilic diseases, chronic obstructive pulmonary disease, as well as inflammatory and immunoregulatory disorders , such as rheumatoid arthritis and atherosclerosis, as well as pain and neurological disorders, such as acute pain, surgical pain, chronic pain and depression and bladder disorders. Furthermore, the present invention relates to the use of a compound of general formula 1 for the treatment and/or prevention of:

(1) Cough such as chronic idiopathic cough or chronic refractory cough, cough associated with asthma, COPD, lung cancer,post-viral infection and idiopathic pulmonary fibrosis and other pulmonary interstitial diseases.

(2) Pulmonary fibrotic diseases such as pneumonitis or interstitial pneumonitis associated with collagenosis, e.g. lupus erythematodes, systemic scleroderma, rheumatoid arthritis, polymyositis and dermatomysitis, idiopathic interstitial pneumonias, such as pulmonary lung fibrosis (IPF), non-specific interstitial pneumonia, respiratory bronchiolitis associated interstitial lung disease, desquamative interstitial pneumonia, cryptogenic orgainizing pneumonia, acute interstitial pneumonia and lymphocytic interstitial pneumonia, lymangioleiomyomatosis, pulmonary alveolar proteinosis, Langerhan's cell histiocytosis, pleural parenchymal fibroelastosis, interstitial lung diseases of known cause, such as interstitial pneumonitis as a result of occupational exposures such as asbestosis, silicosis, miners lung (coal dust), farmers lung (hay and mould), Pidgeon fanciers lung (birds) or other occupational airbourne triggers such as metal dust or mycobacteria, or as a result of treatment such as radiation, methotrexate, amiodarone, nitrofurantoin or chemotherapeutics, or for granulomatous disease, such as granulomatosis with polyangitis, Churg-Strauss syndrome, sarcoidosis, hypersensitivity pneumonitis, or interstitial pneumonitis caused by different origins, e.g. aspiration, inhalation of toxic gases, vapors, bronchitis or pneumonitis or interstitial pneumonitis caused by heart failure, X-rays, radiation, chemotherapy, M. boeck or sarcoidosis, granulomatosis, cystic fibrosis or mucoviscidosis, alpha-1-antitrypsin deficiency, acute lung injury as a result of Covid-19/SARS-Cov-2 infection or pulmonary fibrosis secondary to Covid-19/SARS-Cov-2 infection.

(3) Other fibrotic diseases such as hepatic bridging fibrosis, liver cirrhosis, non-alcoholic steatohepatitis (NASH), atrial fibrosis, endomyocardial fibrosis, old myocardial infarction, glial scar, arterial stiffness, arthrofibrosis, Dupuytren's contracture, keloid, scleroderma/systemic sclerosis, mediastinal fibrosis, myelofibrosis, Peyronie's disease, nephrogenic systemic fibrosis, retroperitoneal fibrosis, adhesive capsulitis.

(4) Inflammatory, auto-immune or allergic diseases and conditions such as allergic or non-allergic rhinitis or sinusitis, chronic sinusitis or rhinitis, nasal polyposis, chronic rhinosinusitis, acute rhinosinusitis, asthma, pediatric asthma, allergic bronchitis, alveolitis, hyperreactive airways, allergic conjunctivitis, bronchiectasis, adult respiratory distress syndrome, bronchial and pulmonary edema, bronchitis or pneumonitis, eosinophilic cellulites (e.g., Well's syndrome), eosinophilic pneumonias (e.g., Loeffler's syndrome, chronic eosinophilic pneumonia), eosinophilic fasciitis (e. g., Shulman's syndrome), delayed-type hypersensitivity, non-allergic asthma; exercise induced bronchoconstriction; chronic obstructive pulmonary disease (COPD), acute bronchitis, chronic bronchitis, cough, pulmonary emphysema; systemic anaphylaxis or hypersensitivity responses, drug allergies (e.g., to penicillin, cephalosporin), eosinophiliamyalgia syndrome due to the ingestion of contaminated tryptophane, insect sting allergies; autoimmune diseases, such as rheumatoid arthritis, Graves' disease, Sjogren's syndrome psoriatic arthritis, multiple sclerosis, systemic lupus erythematosus, myasthenia gravis, immune thrombocytopenia (adult ITP, neonatal thrombocytopenia, pediatric ITP), immune hemolytic anemia (auto-immune and drug induced), Evans syndrome (platelet and red cell immune cytopaenias), Rh disease of the newborn, Goodpasture's syndrome (anti-GBM disease), Celiac, autoimmune cardio-myopathy juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e. g., necrotizing, cutaneous, and hypersensitivity vasculitis); erythema nodosum; eosinophilic myositis, eosinophilic fasciitis, cancers with leukocyte infiltration of the skin or organs; ophthalmic diseases such as age related macular degeneration, diabetic retinopathy and diabetic macular edema, keratitis, eosinophilic keratitis, keratoconjunctivitis, vernal keratoconjunctivitis, scarring, anterior segment scarring, blepharitis, blepharoconjunctivitis, bullous disorders, cicatricial pemphigoid, conjunctival melanoma, papillary conjunctivitis, dry eye, episcleritis, glaucoma, gliosis, Granuloma annulare, Graves' ophthalmopathy, intraocular melanoma, Pinguecula, proliferative vitreoretinopathy, pterygia, scleritis, uveitis, acute gout flares, gout or osteoarthritis.

(5) Pain such as chronic idiopathic pain syndrome, neuropathic pain, dysesthesia, allodynia, migraine, dental pain and post-surgical pain.

(6) Depression, anxiousness, diabetic neuropathy and bladder disorders such as bladder outlet obstruction, overactive bladder, cystitis; myocardial reperfusion injury or brain ischaemia injury.

In a further aspect the present invention relates to a compound of general formula 1 for use in the treatment and/or prevention of above mentioned diseases and conditions.

In a further aspect the present invention relates to the use of a compound of general formula 1 for the preparation of a medicament for the treatment and/or prevention of above mentioned diseases and conditions.

In a further aspect of the present invention the present invention relates to methods for the treatment or prevention of above mentioned diseases and conditions, which method comprises the administration of an effective amount of a compound of general formula 1 to a human being.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with fibrotic diseases, inflammatory and immunoregulatory disorders, respiratory or gastrointestinal diseases or complaints, inflammatory diseases of the joints or of the nasopharynx, eyes, and skin or conditions such as for example cough, idiopathic pulmonary fibrosis, other pulmonary interstitial diseases, asthma or allergic diseases, eosinophilic diseases, chronic obstructive pulmonary disease, atopic dermatitis as well as autoimmune pathologies, such as rheumatoid arthritis and atherosclerosis, or therapeutic agents useful for the treatment of ophthalmic diseases, pain and depression.

Additional therapeutic agents that are suitable for such combinations include in particular those, which, for example, potentiate the therapeutic effect of one or more active substances with respect to one of the indications mentioned and/or allow the dosage of one or more active substances to be reduced.

Therefore, a compound of the invention may be combined with one or more additional therapeutic agents selected from the group consisting of antifibrotic agents, anti-tussive agents, anti-inflammatory agents, anti-atopic dermatitis agents, analgesics, anti-convulsants, anxiolytics, sedatives, skeletal muscle relaxants or anti-depressants.

Antifibrotic agents are for example nintedanib, pirfenidone, phosphodiesterase-IV (PDE4) inhibitors such as roflumilast, autotaxin inhibitors such as GLPG-1690 or BBT-877; connective tissue growth factor (CTGF) blocking antibodies such as Pamrevlumab; B-cell activating factor receptor (BAFF-R) blocking antibodies such as Lanalumab; alpha-V/beta-6 blocking inhibitors such as BG-00011/STX- 100, recombinant pentraxin-2 (PTX-2) such as PRM-151; c-Jun N-terminal kinase (JNK) inhibitors such as CC-90001; galectin-3 inhibitors such as TD-139; G-protein coupled receptor 84 (GPR84) inhibitors such as GLPG-1205; G-protein coupled receptor 84/ G-protein coupled receptor 40 dual inhibitors such as PBI-4050; Rho Associated Coiled-Coil Containing Protein Kinase 2 (ROCK2) inhibitors such as KD-025; heat shock protein 47 (HSP47) small interfering RNA such as BMS-986263/ND-L02-s0201; Wnt pathway inhibitor such as SM-04646; LD4/PDE3/4 inhibitors such as Tipelukast; recombinant immuno-modulatory domains of histidyl tRNA synthetase (HARS) such as ATYR-1923; prostaglandin synthase inhibitors such as ZL-2102/SAR-191801; 15-hydroxy-eicosapentaenoic acid (15-HEPE e.g. DS-102); Lysyl Oxidase Like 2 (LOXL2) inhibitors such as PAT-1251, PXS-5382/PXS-5338; phosphoinositide 3-kinases (PI3K)/mammalian target of rapamycin (mTOR) dual inhibitors such as HEC-68498; calpain inhibitors such as BLD-2660; mitogen-activated protein kinase kinase kinase (MAP3K19) inhibitors such as MG-S-2525; chitinase inhibitors such as OATD-01; mitogen-activated protein kinase-activated protein kinase 2 (MAPKAPK2) inhibitors such as MMI-0100; transforming growth factor beta 1 (TGF-beta1) small interfering RNA such as TRK250/BNC-1021; or lysophosphatidic acid receptor antagonists such as BMS-986278.

Anti-tussive agents are, for example, purinoceptor 3 (P2X3) receptor antagonists such as gefapixant, S-600918, BAY-1817080, or BLU-5937; neurokinin 1 (NK-1) receptor antagonist such as Orvepitant, Aprepitant; nicotinic acetylcholine receptor alpha 7 subunit stimulator such as ATA-101/bradanicline; codeine, gabapentin, pregablin, or azithromycin. Anti-inflammatory agents are, for example, corticosteroids such as prednisolone or dexamethasone; cyclo-oxygenase-2 (COX2) inhibitors such as celecoxib, rofecoxib, parecoxib, valdecoxib, deracoxib, etoricoxib or lumiracoxib; prostaglandin E2 antagonists; leukotriene B4 antagonists; leukotriene D4 antagonists such as monteleukast; 5-lipoxygenase inhibitors; or other nonsteroidal anti-inflammatory agents (NSAIDs) such as aspirin, diclofenac, diflunisal, etodolac, ibuprofen or indomethacin.

Anti-atopic dermatitis agents are, for example, cyclosporin, methotrexate, mycophenolate mofetil, azathioprine, phosphodiesterase inhibitors (e.g. apremilast, crisaborole), Janus Associated Kinase (JAK) inhibitors (e.g. tofacitinib), neutralizing antibodies against IL-4/IL-13 (e.g. dupilamab), IL-13 (e.g. lebrikizumab, tralokinumab) and IL-31 (nemolizumab).

Analgesics are, for example, of the opioid type, such as morphine, oxymorphine, levopanol, oxycodon, propoxyphene, nalmefene, fentanyl, hydrocondon, hydromorphone, meripidine, methadone, nalorphine, naloxone, naltrexone, buprenorphine, butorphanol, nalbuphine, pentazocine; or of the non-opioid type, such as acetophenamine Anti-depressants are, for example, tricyclic anti-depressants such as amitriptyline, clomipramine, despramine, doxepin, desipramine, imipramine, nortriptyline; selective serotonin reuptake inhibitor anti-depressants (SSRIs) such as fluoxetine, paroxetine, sertraline, citalopram, escitalopram; norepinephrine reuptake inhibitor anti-depressants (SNRIs) such as maprotiline, lofepramine, mirtazapine, oxaprotiline, fezolamine, tomoxetine, mianserin, buproprion, hydroxybuproprion, nomifensine, viloxazine; dual serotonin-norepinephrine reuptake inhibitor anti-depressants (SNRIs) such as duloxetine, venlafaxine, desvenlafaxine, levomilnacipran; atypical antidepressants such as trazodone, mirtazapine, vortioxetine, vilazodone, bupropion; or monoamine oxidase inhibitor anti-depressantss (MAOIs) such as tranylcypromine, phenelzine, or isocarboxazid.

Anxiolytics are, for example, benzodiazepines such as alprazolam, bromazepam, chlordiazepoxide, clonazepam, clorazepate, diazepam, flurazepam, lorazepam, oxazepam, temazepam, triazolam, or tofisopam; or they are nonbenzodiazepine hypnoticssuch as eszopiclone, zaleplon, zolpidem, or zopiclone; or they are carbamates e.g. meprobamate, carisoprodol, tybamate, or lorbamate; or they are antihistamines such as hydroxyzine, chlorpheniramine or diphenhydramine.

Sedatives are, for example, barbiturate sedatives, such as amobarbital, aprobarbital, butabarbital, butabital, mephobarbital, metharbital, methohexital, pentobarbital, secobarbital, talbutal, theamylal, or thiopental; or they are non-barbiturate sedatives such as glutethimide, meprobamate, methaqualone or dichloalphenazone.

Skeletal muscle relaxants are, for example, baclofen, meprobamate, carisoprodol, cyclobenzaprine, metaxalone, methocarbamol, tizanidine, chlorzoxazone or orphenadrine. Other suitable combination partners are inhibitors of Acetylcholinesterase inhibitors such as donepezil; 5-HT-3 anatgonists such as ondansetron; metabotropic glutamate receptor antagonists; antiarrhythmics such as mexiletine or phenytoin; or NMDA receptor antagonists.

Further suitable combination partners are incontinence medications, for example, anticholinergics such as oxybutynin, tolterodine, darifenacin, fesoterodine, solifenacin or trospium; or they are bladder muscle relaxants such as mirabegron; or they are alpha blockers such as tamsulosin, alfuzosin, silodosin, doxazosin or terazosin.

The dosage for the combination partners mentioned above is usually ⅕ of the lowest dose normally recommended up to 1/1 of the normally recommended dose.

Therefore, in another aspect, this invention relates to the use of a compound according to the invention in combination with one or more additional therapeutic agents described hereinbefore and hereinafter for the treatment of diseases or conditions which may be affected or which are mediated by TRPA1, in particular diseases or conditions as described hereinbefore and hereinafter.

In a further aspect this invention relates to a method for treating a disease or condition which can be influenced by the inhibition of TRPA1 in a patient that includes the step of administering to the patient in need of such treatment a therapeutically effective amount of a compound of formula (I) or a pharmaceutically acceptable salt thereof in combination with a therapeutically effective amount of one or more additional therapeutic agents.

In a further aspect this invention relates to the use of a compound of formula (I) or a pharmaceutically acceptable salt thereof in combination with one or more additional therapeutic agents for the treatment of diseases or conditions which can be influenced by the inhibition of TRPA1 in a patient in need thereof.

In yet another aspect the present invention relates to a method for the treatment of a disease or condition mediated by TRPA1 activity in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter.

The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts. Consequently, in another aspect, this invention relates to a pharmaceutical composition that comprises a compound according to the invention and one or more additional therapeutic agents described hereinbefore and hereinafter, optionally together with one or more inert carriers and/or diluents.

In yet another aspect the present invention relates to the use of a compound according to the invention in a cough-measuring device.

Other features and advantages of the present invention will become apparent from the following more detailed examples which illustrate, by way of example, the principles of the invention.

Preparation

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used.

The general processes for preparing the compounds according to the invention will become apparent to the one skilled in the art studying the following schemes. Any functional groups in the starting materials or intermediates may be protected using conventional protecting groups. These protecting groups may be cleaved again at a suitable stage within the reaction sequence using methods familiar to the one skilled in the art.

The compounds according to the invention are prepared by the methods of synthesis described hereinafter in which the substituents of the general formulae have the meanings given herein before. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis. Abbreviations are as defined in the Examples section.

Scheme 1

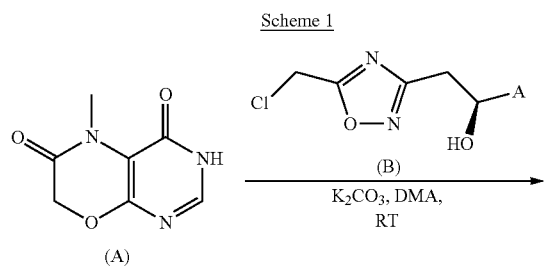

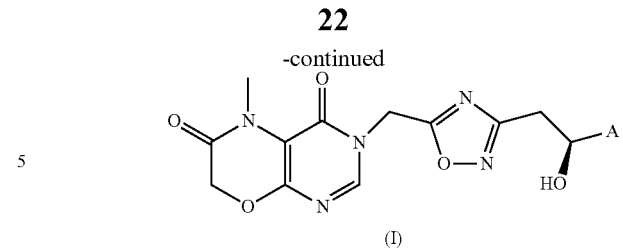

In scheme 1, compounds of formula I can be synthesized via N-alkylation of the intermediate (A) with chloromethylen-oxadiazoles (B) in presence of a base such as potassium carbonate.

Scheme 2

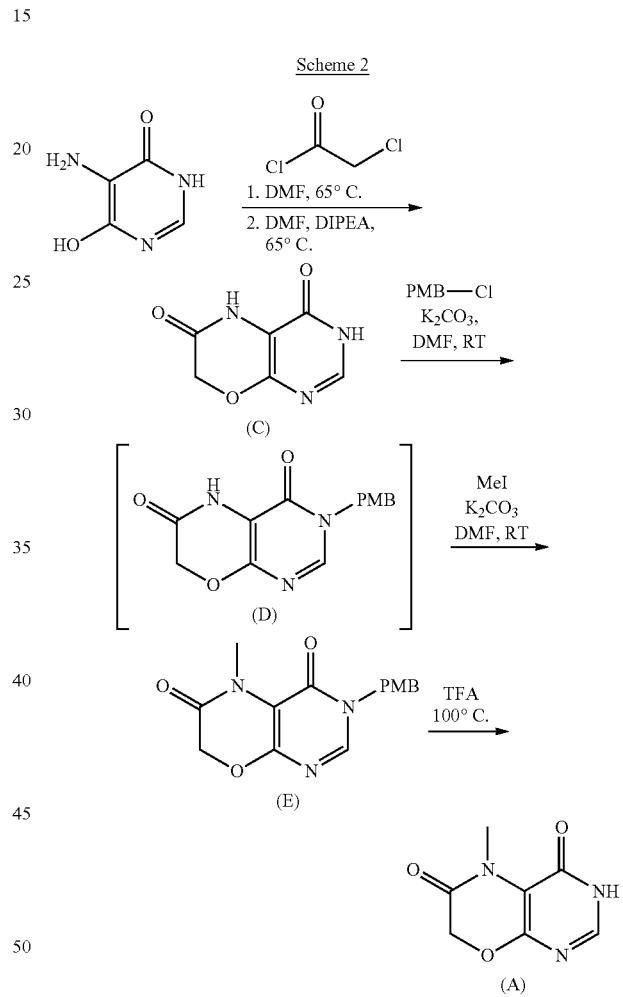

In scheme 2, amidation of 5-aminopyrimidine-4,6-diol with activated acetic acid carrying a leaving group in alpha position (e.g. chloro-acetylchloride) and subsequent cyclisation in presence of a base (e.g. DIPEA) yields (C). N-Alkylation of the pyrimidone (C) with a protecting group such as para-methoxybenzyl can be achieved by treating (C) with an appropriate reagent carrying a leaving group (e.g. para-methoxybenzyl chloride, PMB-Cl) in presence of a base (e.g. $K_2CO_3$). This allows subsequent N-methylation (e.g. with MeI) of (D) in presence of a base (e.g. $K_2CO_3$) to give (E). Finally, cleavage of the protecting group of (E) under suitable conditions (e.g. for PMB: trifluoroacetic acid, 100° C.) gives intermediate (A).

Scheme 3

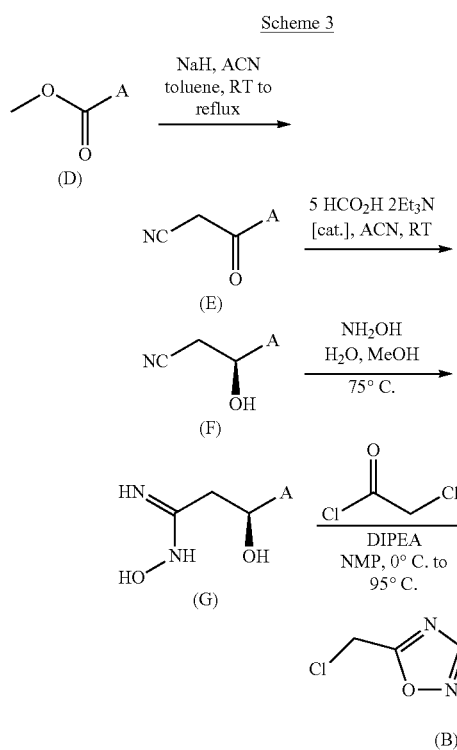

In scheme 3, alpha-cyano ketones (E), synthesized from carboxylic esters (D), are reduced enantioselectively by using an appropriate catalytic systems using a transition metal complex (of e.g. Ru or Ir) in combination with a chiral ligand (e.g. [(1S,2S)-2-amino-1,2-diphenylehtyl](4-toluene-sulfonyl)amido) and a hydrogen source such as formic acid triethylamine complex to provide alcohols (F). Hydroxylamine is added to these alcohols (F) to provide the dihydroxy-propanimidamides (G). Ring-closure to chloromethylen-oxadiazoles (B) can be achieved by stirring the reaction mixture together with chloro acetyl chloride in presence of a base such as DIPEA.

EXAMPLES

Preparation

The compounds according to the invention and their intermediates may be obtained using methods of synthesis which are known to the one skilled in the art and described in the literature of organic synthesis for example using methods described in "Comprehensive Organic Transformations", 2nd Edition, Richard C. Larock, John Wiley & Sons, 2010, and "March's Advanced Organic Chemistry", 7th Edition, Michael B. Smith, John Wiley & Sons, 2013. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled artisan but are not described in detail herein may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner Before the reaction is carried out, any corresponding functional groups in the starting compounds may be protected using conventional protecting groups. These protecting groups may be cleaved again at a suitable stage within the reaction sequence using methods familiar to the skilled man and described in the literature for example in "Protecting Groups", 3rd Edition, Philip J. Kocienski, Thieme, 2005, and "Protective Groups in Organic Synthesis", 4th Edition, Peter G. M. Wuts, Theodora W. Greene, John Wiley & Sons, 2006. The terms "ambient temperature" and "room temperature" are used interchangeably and designate a temperature of about 20° C., e.g. between 19 and 24° C.

Abbreviations

| | |
|---|---|
| ACN | acetonitrile |
| Aq. | Aqueous |
| ° C. | Degree Celsius |
| CyH/CH | cyclohexane |
| conc. | Concentrated |
| DCM | dichloro methane |
| DIPEA | N,N-diisopropylethylamine |
| DMA | N,N-dimethylacetamide |
| DMF | N,N-dimethylformamide |
| DMSO | dimethyl sulfoxide |
| ESI-MS | Electrospray ionisation mass spectrometry |
| EtOAc | ethyl acetate |
| EtOH | ethanol |
| ex | example |
| eq | equivalent |
| FA | formic acid |
| h | hour |
| HCl | Hydrochloric acid |
| HPLC | High performance liquid chromatography |
| $K_2CO_3$ | potassium carbonate |
| L | liter |
| LiOH*$H_2O$ | Lithium hydroxide monohydrate |
| M | molar |
| MeOH | methanol |
| $MgSO_4$ | magnesium sulphate |
| min | minute |
| mL | milliliter |
| MTBE | tert-butylmethylether |
| $NH_3$ | ammonia |
| NMP | N-Methyl-2-pyrrolidon |
| PE | Petrol ether |
| PMB | Para-methoxy benzyl |
| Prep. | preparative |
| RP | Reversed phase |
| RT | room temperature (about 20° C.) |
| sat. | saturated |
| TBTU | Benzotriazolyl tetramethyluronium tetrafluoroborate |
| TEA | triethylamine |
| TFA | trifluoroacetic acid |
| TFAA | trifluoroacetic anhydride |
| THF | tetrahydrofuran |

Preparation of Intermediates

Intermediate I

Intermediate I.1 (General Route)

(3S)-3-(4-chlorophenyl)-3-hydroxypropanenitrile

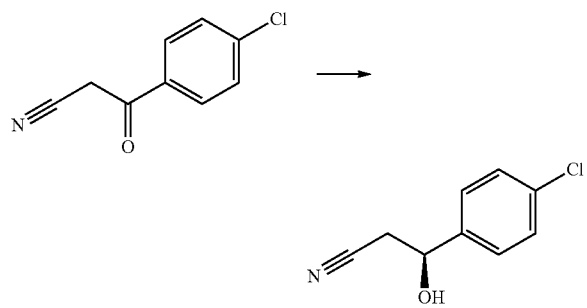

10.0 g (55.7 mmol) 4-Chlorobenzoylacetonitrile are added to 100 mL ACN under inert atmosphere. 142 mg (0.23 mmol) Chloro([(1S ,2S)-2-amino-1,2-diphenylethyl](4-toluenesulfonyl)amido)(mesitylene)ruthenium (II) (CAS 174813-81-1) are added, followed by dropwise addition of 8.30 mL (19.8 mmol) formic acid triethylamine complex (5:2).

After stirring at RT for 3 h, the solvent is removed in vacuo. To the remaining crude mixture is added water and this mixture is extracted two times with EtOAc. The organic layers are combined, dried over $MgSO_4$, filtered, and the solvent is removed in vacuo to provide intermediate I.1.

| | |
|---|---|
| $C_9H_8ClNO$ | (M = 181.6 g/mol) |
| ESI-MS: | 226 [M + HCOO]$^-$ |
| $R_t$ (HPLC): | 0.81 min (method B) |

The following compounds are prepared using procedures analogous to those described for intermediate I.1 using appropriate starting materials. As is appreciated by those skilled in the art, these analogous examples may involve variations in general reaction conditions.

| Int. | Starting materials | Structure | ESI-MS | HPLC retention time [min] (method), or 1H NMR (300 MHz, DMSO-d6) ppm |
|---|---|---|---|---|
| I.2 | (4-methylphenyl cyanoacetyl) | (3S)-3-(4-methylphenyl)-3-hydroxypropanenitrile | 184 [M + Na]$^+$ | 0.76 (B) |
| I.3 | (4-iodophenyl cyanoacetyl) | (3S)-3-(4-iodophenyl)-3-hydroxypropanenitrile | 256 [M + H − H$_2$O]$^+$ | 0.84 (B) |
| I.4 | IV.1 | (benzothiophene-F derivative) | 266 [M + HCOO]$^-$ | 3.03 (E) |
| I.5 | (benzothiophene ketone) | (benzothiophene alcohol) | — | δ 7.98-7.91 (m, 1 H), 7.82-7.77 (m, 1 H), 7.37-7.31 (m, 3 H), 6.56 (d, J = 5.0 Hz, 1 H), 5.28-5.20 (m, 1 H), 3.14-2.94 (m, 2 H) |
| I.6 | IV.2 | (5-chlorobenzofuran alcohol) | 266 [M + HCOO]$^-$ | 3.12 (E) |
| I.7 | IV.3 | (5-fluorobenzofuran alcohol) | — | δ 7.63-7.56 (m, 1 H), 7.46 (dd, J = 8.9, 2.7 Hz, 1 H), 7.14 (td, J = 9.2, 2.7 Hz, 1 H), 6.88 (s, 1 H), 6.41 (d, J = 5.5 Hz, 1 H), 5.10-5.01 (m, 1 H), 3.16-2.98 (m, 2 H) |

Intermediate II

Intermediate II.1 (General Route)

(3S)-3-(4-chlorophenyl)-N,3-dihydroxypropanimidamid1

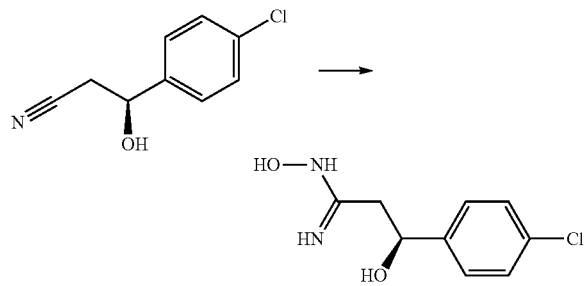

To 9.82 g (54.1 mmol) (3S)-3-(4-chlorophenyl)-3-hydroxypropanenitrile (intermediate I.1) in 100 mL MeOH are added 8.00 mL (136 mmol) hydroxylamine (50% in water) and the mixture is stirred at 75° C. for 1.5 h. After cooling to RT, all volatiles are removed in vacuo to yield the crude product, which is used without further purification.

| $C_9H_{11}ClN_2O_2$ | (M = 214.6 g/mol) |
|---|---|
| ESI-MS: | 215 $[M + H]^+$ |
| $R_t$ (HPLC): | 0.60 min (method B) |

The following compounds are prepared using procedures analogous to those described for intermediate II.1 using appropriate starting materials. As is appreciated by those skilled in the art, these analogous examples may involve variations in general reaction conditions.

| Int. | Starting materials | Structure | ESI-MS | HPLC retention time [min] (method) |
|---|---|---|---|---|
| II.2 | I.2 | 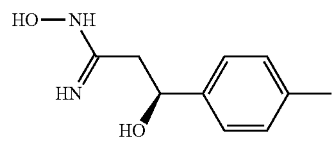 | 195 $[M + H]^+$ | 0.57 (B) |
| II.3 | I.3 | 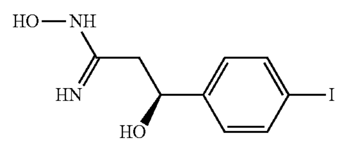 [SMILES: N=C(C[C@H](O)c1ccc(I)cc1)NO] | 307 $[M + H]^+$ | 0.71 (B) |
| II.4 | I.4 | 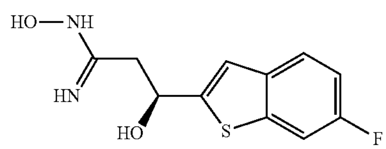 [SMILES: N=C(C[C@H](O)c1cc2ccc(F)cc2s1)NO] | 255 $[M + H]^+$ | 2.07 (E) |
| II.5 | I.5 | 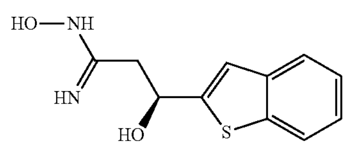 [SMILES: N=C(C[C@H](O)c1cc2ccccc2s1)NO] | 237 $[M + H]^+$ | 1.93 (E) |
| II.6 | I.6 | 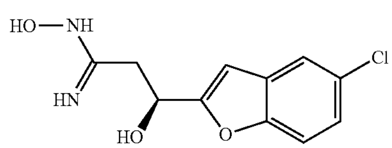 [SMILES: N=C(C[C@H](O)c1cc2cc(Cl)ccc2o1)NO] | 255 $[M + H]^+$ | 2.18 (E) |
| II.7 | I.7 | 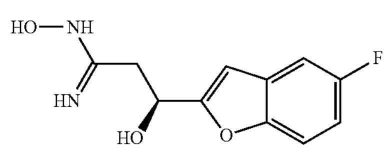 [SMILES: N=C(C[C@H](O)c1cc2cc(F)ccc2o1)NO] | 239 $[M + H]^+$ | 1.90 (E) |

Intermediate III

Intermediate III.1 (General Route)

(1S)-2-[5-(chloromethyl)-1,2,4-oxadiazol-3-yl]-1-(4-chlorophenyl)ethan-1-ol

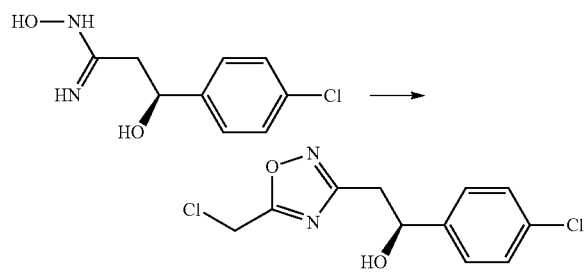

To 11.2 g (52.4 mmol) of intermediate II.1 in 55 mL NMP are added 10.0 mL (57.8 mmol) DIPEA. The mixture is cooled to 0° C. before 4.60 mL (57.7 mmol) chloroacetyl chloride dissolved in 5 mL NMP are slowly added and the mixture is stirred at 0° C. for 45 min. The mixture is then heated up to 95° C. and stirring is continued for 4 h. After cooling down to RT, 200 mL water are added and the resulting mixture is extracted three times with EtOAc. The organic layers are combined, dried over MgSO$_4$, filtered and the solvent is removed in vacuo. The residue is purified by column chromatography (silica gel; PE/EtOAc, 7/3).

| | |
|---|---|
| $C_{11}H_{10}Cl_2N_2O_2$ | (M = 273.1 g/mol) |
| ESI-MS: | 271 [M − H]$^-$ |
| R$_t$ (HPLC): | 0.93 min (method B) |

The following compounds are prepared using procedures analogous to those described for intermediate III.1 using appropriate starting materials. As is appreciated by those skilled in the art, these analogous examples may involve variations in general reaction conditions.

| Int. | Starting materials | Structure | ESI-MS | HPLC retention time [min] (method) |
|---|---|---|---|---|
| III.2 | II.2 | 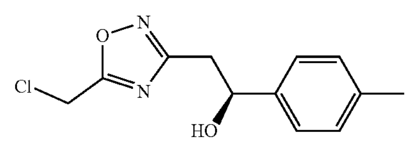 [SMILES: Cc1ccc([C@@H](O)Cc2noc(CCl)n2)cc1] | 251 [M − H]$^-$ | 0.92 (C) |
| III.3 | II.3 | 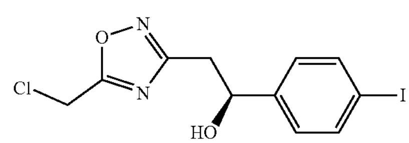 [SMILES: O[C@@H](Cc1noc(CCl)n1)c1ccc(I)cc1] | 387 [M + Na]$^+$ | 1.01 (B) |
| III.4 | II.4 | 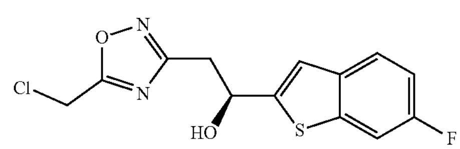 [SMILES: O[C@@H](Cc1noc(CCl)n1)c1cc2ccc(F)cc2s1] | 251 [M − H]$^-$ | 6.02 (F) |
| III.5 | II.5 | 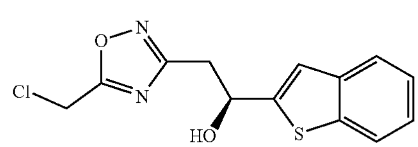 [SMILES: O[C@@H](Cc1noc(CCl)n1)c1cc2ccccc2s1] | 295 [M + H]$^+$ | 5.88 (F) |
| III.6 | II.6 | 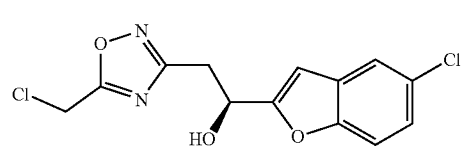 [SMILES: O[C@@H](Cc1noc(CCl)n1)c1cc2cc(Cl)ccc2o1] | 311 [M − H]$^-$ | 6.12 (F) |
| III.7 | II.7 | 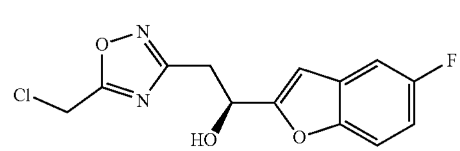 [SMILES: O[C@@H](Cc1noc(CCl)n1)c1cc2cc(F)ccc2o1] | 295 [M − H]$^-$ | 5.67 (F) |

Intermediate IV

Intermediate IV.1 (General Route)

3-(6-fluoro-1-benzothiophen-2-yl)-3-oxopropanenitrile

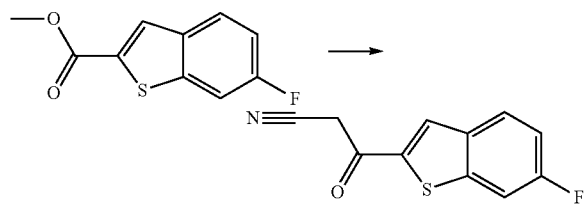

To 0.63 g (3.00 mmol) methyl 6-fluoro-1-benzothiophene-2-carboxylate in 9.0 mL dry toluene and 0.78 mL dry ACN are added 0.36 g (9.00 mmol) of NaH (60% in oil) under inert atmosphere at RT. The mixture is heated to reflux and stirred for 16 h, cooled to room temperature, poured on ice/water (30 mL), and treated with 2M HCl to reach pH=1. EtOAc (20 mL) is added and the phases are separated. The aqueous phase is extracted once more with EtOAc (20 mL), the combined organic phases are washed with brine (20 mL), and the solvent is removed under reduced pressure. The crude product is purified by silica gel column chromatography using a gradient of EtOAc/hexane (30% to 40%).

| | |
|---|---|
| $C_{11}H_6FNOS$ | (M = 219.23 g/mol) |
| ESI-MS: | 218 [M − H]⁻ |
| $R_t$ (HPLC): | 3.31 min (E) |

The following compounds are prepared using procedures analogous to those described for intermediate IV.1 using appropriate starting materials. As is appreciated by those skilled in the art, these analogous examples may involve variations in general reaction conditions.

| Int. | Starting materials | Structure | ESI-MS | HPLC retention time [min] (method) |
|---|---|---|---|---|
| IV.2 | ![](Cl-benzofuran methyl ester) | ![](Cl-benzofuran oxopropanenitrile) | 218 [M − H]⁻ | 3.33 (E) |
| IV.3 | ![](F-benzofuran methyl ester) | ![](F-benzofuran oxopropanenitrile) | 202 [M − H]⁻ | 3.08 (E) |

Intermediate V 3H,4H,5H,6H,7H-pyrimido[4,5-b][1,4]oxazine-4,6-dione

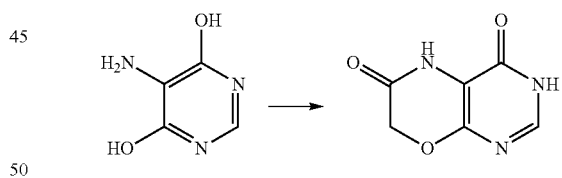

To 10.0 g (127.10 mmol) 5-aminopyrimidine-4,6-diol in 300 mL DMF is slowly added 7.5 mL (94.41 mmol) chloroacetyl chloride under stirring at 65° C. After stirring at 65° C. for 1.5 h, 36.1 mL (129.94 mmol) DIPEA are slowly added to the reaction mixture and stirring at 65° C. is continued for 45 min. The reaction mixture is concentrated under reduced pressure, treated with water, and the precipitated product is filtered, washed with small io amounts of EtOH, and dried.

| | |
|---|---|
| $C_6H_5N_3O_3$ | (M = 167.1 g/mol) |
| ESI-MS: | 168 [M + H]⁺ |
| $R_t$ (HPLC): | 0.20 min (method G) |

Intermediate VI

3-[(4-methoxyphenyl)methyl]-5-methyl-3H,4H,5H,6H,7H-pyrimido[4,5-b][1,4]oxazine-4,6-dione

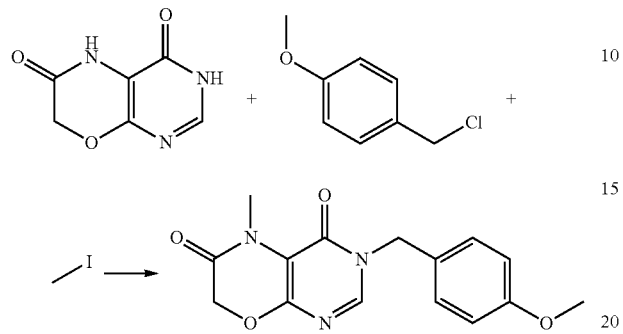

680 mg (4.07 mmol) 3H,4H,5H,6H,7H-pyrimido[4,5-b][1,4]oxazine -4,6 -dione (intermediate V) in 15 mL DMF is treated with 843 mg (6.10 mmol) potassium carbonate and is stirred at RT for 15 min. 0.58 mL (4.27 mmol) 1-(chloromethyl)-4-methoxybenzene is added and the reaction mixture is stirred for 20 h. 843 mg (6.10 mmol) potassium carbonate and 0.30 ml (4.88 mmol) methyl iodide are added and the reaction mixture is stirred at RT for 20 h. 0.26 ml (4.07 mmol) methyl iodide is added and the reaction mixture is stirred at RT for 20 h, filtered, concentrated under reduced pressure, and purified by reversed phase HPLC (ACN/H$_2$O gradient, 0.1% TFA).

| $C_{15}H_{15}N_3O_4$ | (M = 301.3 g/mol) |
|---|---|
| ESI-MS: | 302 [M + H]$^+$ |
| R$_t$ (HPLC): | 0.95 min (method B) |

Intermediate VII 5-methyl-3H,4H,5H,6H,7H-pyrimido[4,5-b][1,4]oxazine-4,6-dione

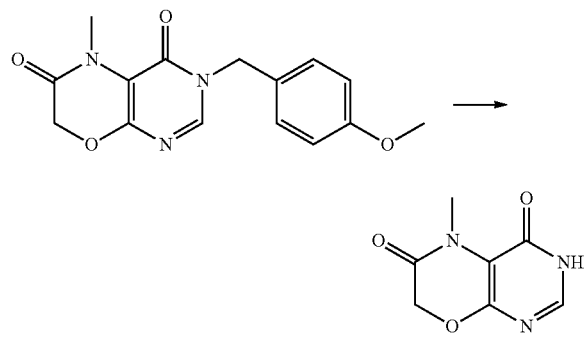

5.30 g (14.07 mmol) 3-[(4-methoxyphenyl)methyl]-5-methyl-3H,4H,5H,6H,7H-pyrimido[4,5-b][1,4]oxazine-4,6-dione (intermediate VI) is treated with 16 ml TFA and stirred at 100° C. for 1.5 h. Afterwards, the reaction mixture is stirred in the microwave at 120° C. for 15 min, poured onto iced water and filtered. The filtrate is lyophilized and directly used without further purification.

| $C_7H_7N_3O_3$ | (M = 181.2 g/mol) |
|---|---|
| ESI-MS: | 182 [M + H]$^+$ |
| R$_t$ (HPLC): | 0.37 min (method B) |

Preparation of Final Compounds

Example 1 (General Procedure)

3-({3-[(2S)-2-(4-chlorophenyl)-2-hydroxyethyl]-1,2,4-oxadiazol-5-yl}methyl)-5-methyl-3H,4H,5H,6H,7H-pyrimido[4,5-b][1,4]oxazine-4,6-dione

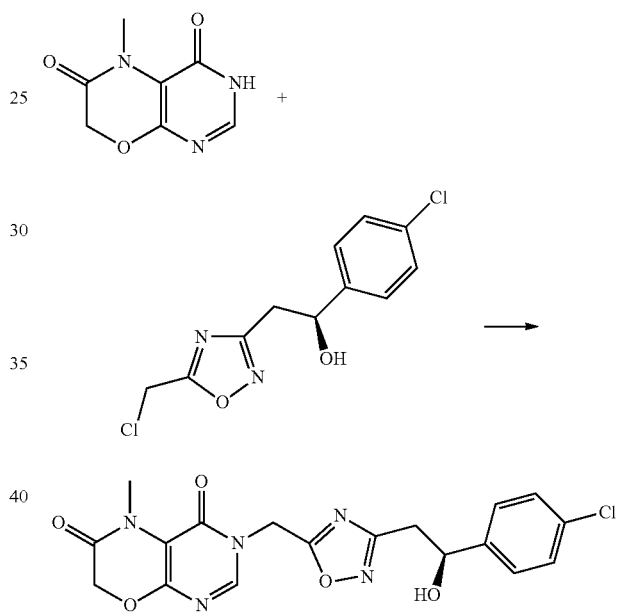

A mixture of 30 mg (0.11 mmol) intermediate VII, 20 mg (0.11 mmol) intermediate III.1, and 30 mg (0.22 mmol) K$_2$CO$_3$ in 1.0 mL DMF is stirred at RT for 1 h. The reaction mixture is filtered and the filtrate is purified by reversed phase HPLC (ACN/H$_2$O gradient, 0.1% TFA) to yield the desired product.

| $C_{18}H_{16}ClN_5O_4$ | (M = 417.80 g/mol) |
|---|---|
| ESI-MS: | 418 [M + H]$^+$ |
| R$_t$ (HPLC): | 0.44 min (method A) |

$^1$H NMR (400 MHz, DMSO-d$_6$) δ ppm: 2.90-3.10 (m, 2 H), 3.33 (s, 3 H), 4.82 (s, 2 H), 4.96 (dd, J=7.9, 5.7 Hz, 1 H), 5.48 (s, 2 H), 7.32-7.39 (m, 4 H), 8.44 (s, 1 H)

The following compounds are prepared using procedures analogous to those described for example 1 general procedure, using appropriate starting materials. As is appreciated by those skilled in the art, these analogous examples may involve variations in general reaction conditions.

| Ex. | Starting materials | Structure | Reaction conditions |
|---|---|---|---|
| 2 | VII + III.4 | [structure: methyl-pyrimido-oxazinone linked via CH2-oxadiazole-CH2-CH(OH)- to 6-fluorobenzothiophene] | 1.05 eq int III.4; 2.0 eq. K₂CO₃; DMF, RT, 3.5 h |
| 3 | VII + III.5 | [structure: methyl-pyrimido-oxazinone linked via CH2-oxadiazole-CH2-CH(OH)- to benzothiophene] | 1.05 eq int III.5; 2.0 eq. K₂CO₃; DMF, RT, 3 h |
| 4 | VII + III.7 | [structure: methyl-pyrimido-oxazinone linked via CH2-oxadiazole-CH2-CH(OH)- to 5-fluorobenzofuran] | 1.05 eq int III.7; 2.0 eq. K₂CO₃; DMF, RT, 3 h |
| 5 | VII + III.3 | [structure: methyl-pyrimido-oxazinone linked via CH2-oxadiazole-CH2-CH(OH)- to 4-iodophenyl] | 1.05 eq int III.3; 3.0 eq. K₂CO₃; DMA, RT, 18 h |
| 6 | VII + III.6 | [structure: methyl-pyrimido-oxazinone linked via CH2-oxadiazole-CH2-CH(OH)- to 5-chlorobenzofuran] | 1.05 eq int III.6; 2.0 eq. K₂CO₃; DMF, RT, 3 h |
| 7 | VII + III.2 | [structure: methyl-pyrimido-oxazinone linked via CH2-oxadiazole-CH2-CH(OH)- to 4-methylphenyl] | 1.0 eq int III.2; 3.0 eq. K₂CO₃; DMA, RT, 18 h |

Analytical data for the compounds described in the table above:

| Ex. | ESI-MS | HPLC retention time [min] (method) | ¹H NMR (400 MHz, DMSO-d₆) δ ppm |
|---|---|---|---|
| 2 | 458 [M + H]⁺ | 0.49 (H) | 3.12-3.22 (m, 2 H), 3.32 (s, 3 H), 4.81 (s, 2 H), 5.28 (t, J = 6.7 Hz, 1 H), 5.50 (s, 2 H), 7.21 (td, J = 9.1, 2.5 Hz, 1 H), 7.25 (s, 1 H), 7.75 (dd, J = 8.7, 5.3 Hz, 1 H), 7.82 (dd, J = 9.4, 2.5 Hz, 1 H), 8.44 (s, 1 H). |
| 3 | 440 [M + H]⁺ | 0.68 (D) | 3.18 (d, J = 7.1 Hz, 2 H), 3.32 (s, 3 H), 4.81 (s, 2 H), 5.31 (t, J = 6.7 Hz, 1 H), 5.50 (s, 2 H), 7.25 (s, 1 H), 7.32 (quind, J = 7.2, 1.3 Hz, 2 H), 7.68-7.78 (m, 1 H), 7.90 (d, J = 7.4 Hz, 1 H), 8.45 (s, 1 H) |
| 4 | 442 [M + H]⁺ | 0.45 (A) | 3.14-3.29 (m, 2 H), 3.31 (s, 3 H), 4.81 (s, 2 H), 5.10 (dd, J = 8.1, 5.6 Hz, 1 H), 5.48 (s, 2 H), 6.78 (s, 1 H), 7.10 (td, J = 9.2, 2.7 Hz, 1 H), 7.39 (dd, J = 8.9, 2.7 Hz, 1 H), 7.56 (dd, J = 9.0, 4.2 Hz, 1 H), 8.42 (s, 1 H) |
| 5 | 510 [M + H]⁺ | 0.49 (A) | 2.89-3.06 (m, 2 H), 3.33 (s, 3 H), 4.82 (s, 2 H), 4.92 (dd, J = 7.8, 5.8 Hz, 1 H), 5.48 (s, 2 H), 7.13-7.19 (m, 2 H), 7.63-7.69 (m, 2 H), 8.44 (s, 1 H) |

-continued

| Ex. | ESI-MS | HPLC retention time [min] (method) | $^1$H NMR (400 MHz, DMSO-d$_6$) δ ppm |
|---|---|---|---|
| 6 | 458 [M + H]$^+$ | 0.49 (A) | 3.13-3.30 (m, 2 H), 3.30 (s, 3 H), 4.81 (s, 2 H), 5.10 (dd, J = 7.9, 5.7 Hz, 1 H), 5.48 (s, 2 H), 6.78 (s, 1 H), 7.29 (dd, J = 8.7, 2.2 Hz, 1 H), 7.57 (d, J = 8.7 Hz, 1 H), 7.66 (d, J = 2.2 Hz, 1 H), 8.42 (s, 1 H) |
| 7 | 398 [M + H]$^+$ | 0.42 (A) | 2.87-3.06 (m, 2 H), 3.33 (s, 3 H), 4.82 (s, 2 H), 4.91 (dd, J = 8.2, 5.5 Hz, 1 H), 5.48 (s, 2 H), 7.10 (d, J = 7.9 Hz, 2 H), 7.22 (d, J = 8.0 Hz, 2 H), 8.44 (s, 1 H) |

Analytical HPLC Methods

Method A

| time (min) | Vol % water (incl. 0.1% TFA) | Vol % ACN | Flow [mL/min] |
|---|---|---|---|
| 0.00 | 99 | 1 | 1.6 |
| 0.02 | 99 | 1 | 1.6 |
| 1.00 | 0 | 100 | 1.6 |
| 1.10 | 0 | 100 | 1.6 |

Analytical column: XBridge BEH C18_2.1×30 mm, 1.7 µm; column temperature: 60° C.

Method B

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stable Bond (Agilent) 1.8 µm; 3.0×30 mm; column temp: 60° C.

Method C

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Sunfire (Waters) 2.5 µm; 3.0×30 mm; column temperature: 60° C.

Method D

| Gradient/Solvent Time [min] | Vol % water (incl. 0.1% TFA) | Vol.-% ACN (incl. 0.08% TFA) | Flow [ml/min] |
|---|---|---|---|
| 0.0 | 95.0 | 5.0 | 1.5 |
| 1.3 | 0.0 | 100.0 | 1.5 |
| 1.5 | 0.0 | 100.0 | 1.5 |
| 1.6 | 95.0 | 5.0 | 1.5 |

Preparative column: Sunfire (Waters) C18_3.0×30 mm_2.5 µm; column temperature: 60° C.

Method E

| Gradient/Solvent Time [min] | Vol % water (incl. 0.1% FA) | Vol % CAN (incl. 0.1% FA) | Flow [ml/min] |
|---|---|---|---|
| 0.01 | 95 | 5 | 0.5 |
| 4.00 | 5 | 95 | 0.5 |
| 5.00 | 5 | 95 | 0.5 |
| 5.20 | 95 | 5 | 0.5 |
| 6.00 | 95 | 5 | 0.5 |

Analytical column: AQUITY UPLC C18_2.1×50 mm_1.8 µm. 100 Å; column temperature: 25° C.

Method F

| Gradient/Solvent Time [min] | Vol % water (incl. 0.1% FA) | Vol % CAN (incl. 0.1% FA) | Flow [ml/min] |
|---|---|---|---|
| 0.00 | 95 | 5 | 0.5 |
| 10.00 | 5 | 95 | 0.5 |
| 10.50 | 5 | 95 | 0.5 |
| 11.00 | 95 | 5 | 0.5 |
| 12.00 | 95 | 5 | 0.5 |

Analytical column: AQUITY UPLC C18_2.1×50 mm_1.8 µm. 100 Å; column temperature: 25° C.

Method G

| time (min) | Vol. % water (incl. 0.1% TFA) | Vol. % ACN | Flow [mL/min] |
|---|---|---|---|
| 0.00 | 97 | 3 | 2.2 |
| 0.2 | 97 | 3 | 2.2 |
| 1.0 | 50 | 50 | 2.2 |
| 1.25 | 0 | 100 | 3.0 |
| 1.9 | 0 | 100 | 3.0 |

Analytical column: Zorbax StableBond (Agilent) C18_3.0×30 mm_1.8 µm; column temperature: 60° C.

Method H

| time (min) | Vol % water (incl. 0.1% TFA) | Vol % ACN | Flow [mL/min] |
|---|---|---|---|
| 0.00 | 99 | 1 | 1.6 |
| 0.02 | 99 | 1 | 1.6 |
| 1.00 | 0 | 100 | 1.6 |
| 1.10 | 0 | 100 | 1.6 |

Analytical column: XBridge Phenyl_2.1×30 mm, 1.7 µm; column temperature: 60° C.

The invention claimed is:

1. A compound according to formula (I)

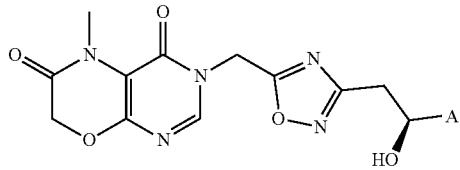

wherein

A is selected from the group consisting of phenyl, thiophenyl, benzofuranyl and benzothiophenyl, and wherein A is unsubstituted or substituted with one or two members of the group $R^1$ selected from the group consisting of halogen and $C_{1-4}$-alkyl;

or a salt thereof.

2. The compound of formula (I) according to claim 1, wherein $R^1$ is selected from the group consisting of F, Cl, I and $CH_3$; or a salt thereof.

3. The compound of formula (I) according to claim 1, wherein A is selected from the group consisting of

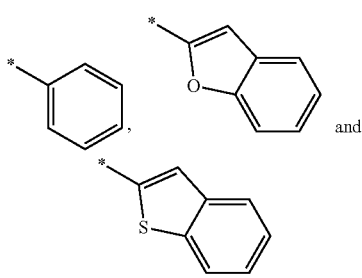

and wherein A is unsubstituted or substituted with one or two members of the group $R^1$; or a salt thereof.

4. The compound according to formula (I) according to claim 1, selected from the group consisting of

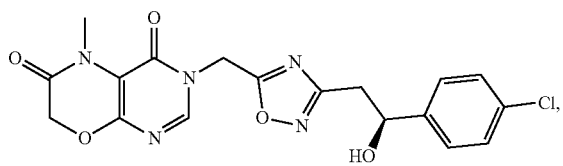

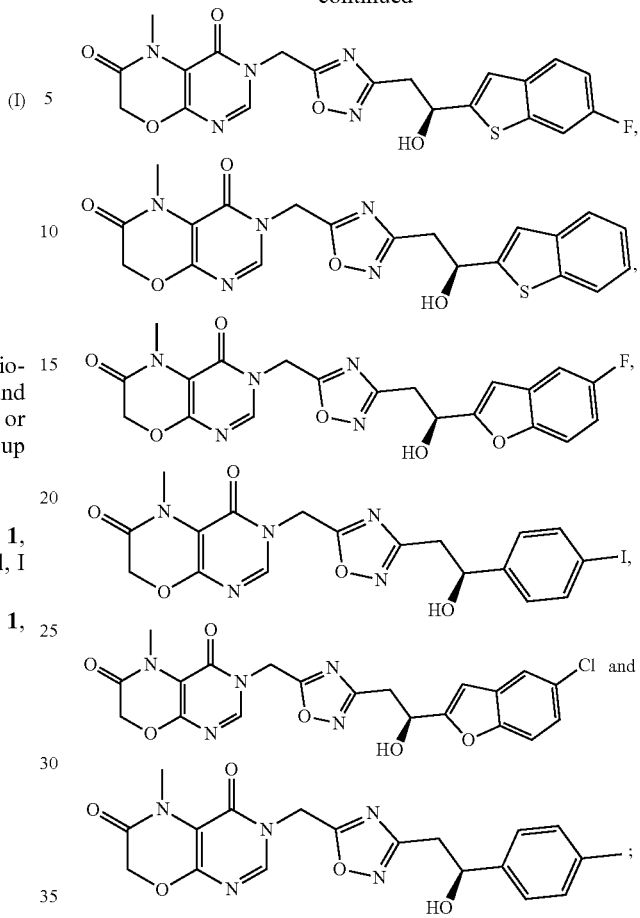

or a salt thereof.

5. A salt of a compound according to claim 1.

6. A pharmaceutically acceptable salt of a compound according to claim 1.

7. A pharmaceutical composition comprising at least one compound of formula (I) according to claim 1, or a pharmaceutically acceptable salt thereof, and one or more pharmaceutically acceptable excipients.

8. A method for the treatment of inflammatory airway diseases, fibrotic diseases or cough in a patient, comprising administering to the patient an effective amount of a compound of formula (I) according to claim 1, or a pharmaceutically acceptable salt thereof.

9. The method according to claim 8 for the treatment of idiopathic pulmonary fibrosis (IPF) or cough.

* * * * *